United States Patent
Nelson et al.

(10) Patent No.: US 11,938,224 B1
(45) Date of Patent: Mar. 26, 2024

(54) BENZONATATE MODIFIED RELEASE SOLID TABLETS AND CAPSULES

(71) Applicant: Tris Pharma, Inc., Monmouth Junction, NJ (US)

(72) Inventors: Andrea Nelson, Belle Mead, NJ (US); Sachin Chaudhari, Monmouth Junction, NJ (US); Nemichand B. Jain, Princeton Junction, NJ (US); Shivanand Puthli, Monmouth Junction, NJ (US)

(73) Assignee: TRIS PHARMA INC, Monmouth Junction, NJ (US)

( * ) Notice: Subject to any disclaimer, the term of this patent is extended or adjusted under 35 U.S.C. 154(b) by 0 days.

(21) Appl. No.: 17/406,137

(22) Filed: Aug. 19, 2021

Related U.S. Application Data

(63) Continuation of application No. 16/777,420, filed on Jan. 30, 2020, now abandoned, which is a continuation of application No. 15/482,201, filed on Apr. 7, 2017, now abandoned.

(60) Provisional application No. 62/320,219, filed on Apr. 8, 2016.

(51) Int. Cl.
*A61K 9/20* (2006.01)
*A61K 9/28* (2006.01)
*A61K 31/24* (2006.01)

(52) U.S. Cl.
CPC .......... *A61K 9/28* (2013.01); *A61K 31/24* (2013.01)

(58) Field of Classification Search
CPC ...... A61K 9/20; A61K 9/2004; A61K 9/2009; A61K 9/2008; A61K 9/2036; A61K 9/2072; A61K 9/2077; A61K 9/2095
See application file for complete search history.

(56) References Cited

U.S. PATENT DOCUMENTS

| | | | |
|---|---|---|---|
| 4,775,694 A | 10/1988 | Press et al. | |
| 6,793,934 B1 | 9/2004 | Burnside et al. | |
| 7,294,347 B2 | 11/2007 | Menjoge et al. | |
| 8,062,667 B2 | 11/2011 | Mehta et al. | |
| 8,202,537 B2 | 6/2012 | Mehta et al. | |
| 8,337,890 B2 | 12/2012 | Mehta et al. | |
| 8,357,398 B2 | 1/2013 | Howard et al. | |
| 8,491,935 B2 | 7/2013 | Mehta et al. | |
| 8,597,684 B2 | 12/2013 | Mehta et al. | |
| 8,747,902 B2 | 6/2014 | Mehta et al. | |
| 8,790,700 B2 | 7/2014 | Mehta et al. | |
| 8,883,217 B2 | 11/2014 | Mehta et al. | |
| 9,180,104 B2 * | 11/2015 | Nelson | A61K 9/2054 |
| 9,180,106 B2 | 11/2015 | Vamvakides | |
| 9,198,864 B2 | 12/2015 | Mehta et al. | |
| 9,408,823 B2 * | 8/2016 | Nelson | A61K 9/209 |
| 9,522,191 B2 | 12/2016 | Mehta et al. | |
| 9,549,989 B2 | 1/2017 | Mehta et al. | |
| 9,675,703 B2 | 6/2017 | Mehta et al. | |
| 9,675,704 B2 | 6/2017 | Mehta et al. | |
| 9,867,797 B2 * | 1/2018 | Nelson | A61K 9/2081 |
| 11,241,411 B2 * | 2/2022 | Nelson | A61K 9/2886 |
| 2005/0136114 A1 | 6/2005 | Kulkarni et al. | |
| 2006/0062844 A1 | 3/2006 | Chenevier et al. | |
| 2008/0176955 A1 | 7/2008 | Heck et al. | |
| 2011/0091509 A1 | 4/2011 | Howard et al. | |
| 2012/0164220 A1* | 6/2012 | Huang | A61K 9/2054 514/282 |
| 2013/0096191 A1 | 4/2013 | Howard et al. | |
| 2014/0271857 A1 | 9/2014 | Nelson et al. | |
| 2014/0272012 A1 | 9/2014 | Gallis et al. | |
| 2016/0008312 A1 | 1/2016 | Nelson et al. | |
| 2016/0310478 A1 | 10/2016 | Mehta et al. | |
| 2017/0100487 A1 | 4/2017 | Mehta et al. | |
| 2017/0274088 A1 | 9/2017 | Mehta et al. | |

FOREIGN PATENT DOCUMENTS

WO   WO-2012/054067   4/2012

OTHER PUBLICATIONS

Ashland, Inc., "Klucel™ hydroxypropylcellulose: Physical and Chemical Properties", LXF Pharm HPC from Ashland Inc., accessed on Nov. 15, 2017 from http://www.ashland.com/file_source/Ashland/Product/Documents/Pharmaceutical/PC_11229_Klucel_HPC.pdf.
Brookfield Engineering Laboratories, "Brookfield DV-II + Viscometer Operating Instructions", accessed on Nov. 15, 2017 from http://www.brookfieldengineering.com/-/media/ametekbrookfield/manuals/lab%20viscometers/dv21%20instructions.pdf?la=en.
Larget, B., "Chapter 3: R Bootstrap Examples", *R Users Guide to Statistics: Unlocking the Power of Data*, Feb. 19, 2014.
M.R.C. Marques, et al., "Simulated Biological Fluids with Possible Application in Dissolution Testing", Dissolution Technologies, pp. 15-28, Aug. 31, 2011.
MedicalLook.com, "Benzonatate review", accessed Nov. 3, 2017 from http://www.medicalook.com/reviews/Benzonatate.html.
Particle Analytical, "BET: Introduction to BET", accessed on Nov. 15, 2017 from http:/particle.dk/methods-analytical-laboratory/surface-area-bet/surface-area-bet-theory/.
Rawle, A., "Basic Principles of Particle Size Analysis", Malvern Instruments Limited, pp. 1-8, 2001.
US Department HHS, FDA—Center for Drug Evaluation and Research, "Guidance for Industry: Statistical Approaches to Establishing Bioequivalence", Jan. 2001.
William, Eni, "Benzonatate (Tessalon Perles, Zonatuss—discontinued in the US)", MedicineNet.com, last reviewed Jun. 2016, accessed Nov. 3, 2017 from https://www.medicinenet.com/benzonatate/article.htm.
Zhang, "Rheological Method for Determining Molecular Weight and Molecular Weight Distribution", Materials Science and Technology, pp. 313-324, Mar. 2012.

(Continued)

*Primary Examiner* — Micah Paul Young
(74) *Attorney, Agent, or Firm* — Howson & Howson LLP; Cathy A. Kodroff

(57) ABSTRACT

A 12-hour anti-tussive modified release solid tablet or tablet-in-capsule is described which comprises a benzonatate-silicon dioxide adsorbate powder in a hydrophilic matrix to provide a 12-hour modified release profile to the benzonatate, wherein there is substantially no benzonatate release from the tablet or capsule in the buccal cavity and no more than about 1% release of the benzonatate within half an hour as determined in an in vitro dissolution assay.

9 Claims, No Drawings

(56) References Cited

OTHER PUBLICATIONS

Ashland, Inc., "Aqualon™ ethylcellulose—Chemistry: Cellulosics", accessed on Nov. 15, 2017 from http://www.ashland.com/industries/pharmaceutical/oral-solid-dose/aqualon-ethylcellulose.
Biogrund.com, "AquaPolish® Fast release coating", accessed on Nov. 17, 2017 from http://www.biogrund.com/products/filmcoating/fast-release/.
Ashland, Inc., "Aquarius™ film coating systems", accessed on Nov. 15, 2017 from http://www.ashland.com/industries/pharmaceutical/oral-solid-dose/aquarius-film-coating systems.
FMC Corporation, "Product Overview: Avicel® PH-102", accessed on Nov. 15, 2017 from http://www.signetchem.com/Content/Upload/z99LA7AvicelPH102NEspec.pdf.
Dow.com, "CARBOWAX™ PEGs for Industrial Applications", accessed on Nov. 15, 2017 from https://www.dow.com/polyglycols/polyethylene/products/carbowaxp.htm#.
Mantrose-Haeuser Co., Inc., "Film Coating: Certiseal® FC 300A", accessed on Nov. 15, 2017 from http://www.mantrose.com/products/pharmaceutical-supplements/film-coatings-for-tablets.
Colorcon, "Expand Your Color Palette (colorant product description)", accessed on Nov. 16, 2017 from https://www.colorcon.com/products-formulation/all-products/nutritional-coatings/colorants.
The Dow Chemical Company, "Ethocel® Technical Handbook", Sep. 2005, accessed on Nov. 16, 2017 from http://msdssearch.dow.com/PublishedLiteratureDOWCOM/db_004f/0901b8038004fb7c.pdf?filepath=/192-00818.pdf&fromPage=GetDoc.
Evonik Industries, "EUDRAGIT® Product Brochure", accessed on Nov. 15, 2017 from http://healthcare.evonik.com/sites/lists/NC/DocumentsHC/Evonik-Eudragit_brochure.pdf.
GalenIQ, "galenIQ™ 720 for Direct Compression", accessed on Nov. 15, 2017 from http://www.galeniq.com/galenIQ_Grades/galenIQ720/.
BASF, "Kollicoat® SR 30 D", accessed on Nov. 15, 2017 from https://pharmaceutical.basf.com/en/Drug-Formulation/Kollicoat-SR-30-D.html.
BASF, "Kollidon® 30—The Original from BASF", accessed on Nov. 15, 2017 from https://pharmaceutical.basf.com/en/Drug-Formulation/Kollidon-30.html.
BASF, "Kollidon® VA64 Fine", accessed on Nov. 15, 2017 from https://pharmaceutical.basf.com/en/Drug-Formulation/Kollidon-VA64-Fine.html.
The Dow Chemical Company, "METHOCEL Cellulose Ethers in Aqueous Systems for Tablet Coating (Product Brochure)", Jul. 2002, accessed on Nov. 15, 2017 from http://msdssearch.dow.com/PublishedLiteratureDOWCOM/dh_004a/0901b8038004ab56.pdf?filepath=/198-00755.pd&fromPage=GetDoc.
The Dow Chemical Company, "Chemistry of Methocel™ Cellulose Ethers—Technical Review", Oct. 2013, accessed on Nov. 16, 2017 from http://msdssearch.dow.com/PublishedLiteratureDOWCOM/dh_08e5/0901b803808e5f58.pdf?filepath=dowwolff/pdfs/noreg/198-02289.pdf&fromPage=GetDoc.

Colorcon, "Opadry® II Complete Aqueous Film Coating System", accessed on Nov. 15, 2017 from https://www.colorcon.com/products-formulation/all-products/film-coatings/immediate-release/opadry-ii.
The Dow Chemical Company, "Polyox Water Soluble Resins (Product Literature)", accessed on Nov. 15, 2017 from http://msdssearch.dow.com/PublishedLiteratureDOWCOM/dh_094e/090168038094e22f.pdf?filepath=/pdfs/noreg/326-00001.pdf&fromPage=GetDoc.
Roquette, "ReadiLycoat (product leaflet)", accessed on Nov. 15, 2017 from https://www.roquette.com/media-center/resources/pharma-leaflet-coating-readilycoat/.
Spectra Colors Corporation, "Food Dyes and Lakes", accessed on Nov. 16, 2017 from http://spectracolors.com/fdc-dyes/.
Colorcon, "Surelease® (product information brochure)", accessed on Nov. 16, 2017 from https://www.colorcon.com/products-formulation/all-products/download/1578/538/34?method=view.
Grace & Co., "Syloid® XDP Silica Pharmaceutical Excipients", accessed on Nov. 16, 2017 from https://grace.com/pharma-and-biotech/en-us/Documents/M458_SyloidXDP_Flyer_final2_HR.pdf.
Pfizer, Inc., "Tessalon® (product label from FDA.org)", revised Dec. 2015, accessed on Nov. 16, 2017 from https://www.accessdata.fda.gov/drugsatfda_docs/label/2011/011210s053lbl.pdf.
RxList.com, "Zonatuss™ (information page)", last reviewed Oct. 30, 2014, accessed Nov. 16, 2017 from https://www.rxlist.com/zonatuss-drug.htm.
Colorcon, "Polyox™ (Application Data)", accessed on Apr. 22, 2020 from https://www.colorcon.com/products-formulation/download/785/2127/34?method=view.
Gupta, et al., "Evaluation of Porous and Non-Porous Solid Carries for Lipid-Based Drug Delivery Systems", GRACE., accessed on Apr. 22, 2020 from https://grace.com/pharma-and-biotech/en-us/Documents/Syloid/PP259_Syloid%20XDP%20Oil%20Adsorption%20Tech%20Poster_rev04LR.pdf.
Docplayer.net, "Huber® Free-Flow Additives (Brochure)", accessed Apr. 22, 2020 from https://docplayer.net/41245495-Huber-free-flow-additives.html.
Sandoval, et al., Comparative analysis of the kinetics of diclofenac sodium release from hydrophilic matrices in conventional and biorelevant dissolution media, Rev. Colomb. Cienc. Quim. Farm. vol. 44(3):282-310, 2015.
Waters, et al., Enhancing the dissolution of phenylbitazone using Syloid® based mesoporus silicas for oral equine applications, Journal of Pharmaceutical Analysis, https://doi.org/10.1016/j.jpha.2018.01.004.
Mehta, et al., U.S. Appl. No. 15/706,234, filed Sep. 15, 2017.
Non-Final Office Action dated Mar. 21, 2018, issued in U.S. Appl. No. 17/482,201.
Response to Non-Final Office Action dated Mar. 21, 2018 filed in U.S. Appl. No. 17/482,201.
Non-Final Office Action dated Aug. 17, 2019 issued in U.S. Appl. No. 17/482,201.
Response to Non-Final Office Action dated Aug. 17, 2019 filed in U.S. Appl. No. 17/482,201.
Non-Final Office Action dated Apr. 3, 2020 issued in U.S. Appl. No. 16/777,420.

* cited by examiner

BENZONATATE MODIFIED RELEASE SOLID TABLETS AND CAPSULES

CROSS-REFERENCE TO RELATED APPLICATIONS

This application is a continuation of U.S. patent application Ser. No. 16/777,420, filed Jan. 30, 2020, which is a continuation of U.S. patent application Ser. No. 15/482,201, filed Apr. 7, 2017, now abandoned, and which claims the benefit of the priority of U.S. Provisional Patent Application No. 62/320,219, filed Apr. 8, 2016, all of which are incorporated herein by reference.

BACKGROUND OF THE INVENTION

Benzonatate is a non-narcotic oral cough suppressant, or antitussive, with therapeutic effects that last about 6 to 8 hours following delivery of an immediate release composition. Its formal name is 2,5,8,11,14,17,20,23,26-nonaoxaoctacosan-28-yl para-butylaminobenzoate. Since it is not an opioid, benzonatate is not prone to potential abuse like some other cough medications such as codeine. See, e.g., U.S. Pat. No. 8,357,398. Benzonatate was approved by the U.S. Food and Drug Administration (FDA) in 1958 for administration as an anti-tussive. [www.medicinenet.com/Benzonatate/article.htm, accessed on Mar. 12, 2013].

Benzonatate is a butylamine, chemically related to other ester local anesthetics such as procaine and tetracaine. Benzonatate is reported to act as a local anesthetic, decreasing the sensitivity of stretch receptors in the lower airway and lung, thereby reducing the drive to cough after taking a deep breath. See, e.g., U.S. Pat. No. 4,775,694. As an antitussive, benzonatate is reported to reduce coughing in various respiratory conditions such as bronchitis, emphysema, influenza, and pneumonia. See, e.g., http://www-.medicalook.com/reviews/Benzonatate.html, accessed on Mar. 12, 2013.

U.S. Pat. No. 8,357,398, WO 2012/054067, US 2013/0096191A1, US 2011/0091509, all Howard et al, describe oral doses forms of benzonatate stated to be useful for anti-tussive applications. Howard et al, describe binding benzonatate to an ion exchange resin for the described purposes of reducing the choking hazard and noxious taste of benzonatate.

U.S. Pat. No. 6,793,934, Burnside et al, describe the use of granulated magnesium aluminometalsilicate alone, or together with dibasic calcium phosphate, to convert a liquid drug such as benzonatate to a powder. The '934 patent describes mixing benzonatate with ethyl alcohol to reduce its viscosity prior to blending with the combination of granulated magnesium aluminometalsilicate and dibasic calcium phosphate, and magnesium stearate. The ethyl alcohol is removed during processing of the resulting powder.

U.S. Pat. No. 4,775,694, Press et al, claim an oil-in-water emulsion with a continuous water phase and a discontinuous oil phase. Essentially all of the benzonatate is present in the discontinuous oil phase of the emulsion.

US Application No. 2008/0176955 A1, Heck et al, describe pharmaceutical compositions containing a combination of benzonatate and guaifenesin which are designed to provide cough relief to opiate-sensitive individuals, including infants and other pediatric patents.

U.S. Pat. No. 9,180,106 and US 2016/0008312 describe solid benzonatate tablets having modified release which is achieved by two different formulations. One tablet formulation contains (a) benzonatate in a matrix which matrix is a homogenous solid dispersion comprising (i) a benzonatate adsorbate and (ii) at least one pharmaceutically acceptable modified release pH-independent, hydrophilic or hydrophobic matrix-forming substance in an amount effective to provide a modified release profile to the benzonatate, and (b) a coating over the benzonatate in a matrix (a), wherein there is no more than about 50%, preferably less than about 40%, more preferably less than about 25%, of the benzonatate released from the composition within 1 hour, about 50% to about 80% of the benzonatate release from the composition within about 6 hours, and not less than about 80% released from the composition at about 12 hours, as determined in an in vitro dissolution test and substantially no benzonatate release from the composition in the buccal cavity or esophagus. A second formulation contains Benzonatate in a drug—ion exchange resin complex having a modified release coating.

Benzonatate is currently commercially available in immediate release form as 100 mg and 200 mg softgel capsules. Initial dose is one 100 mg gelcap by mouth, 3 times a day (8 hour effect). Dosage may be increased as necessary, up to a maximum of 600 mg per day. Benzonatate is also available commercially as a hard gelatin capsule at dose of 150 mg [Zonatuss]. Due to its potency and potential toxicity, the capsules must be swallowed intact in order to avoid release of the medication in the mouth. Excessive absorption of benzonatate (a local anesthetic) in the oral mucosa will result in the rapid development of numbness of the mouth and throat. In extreme cases, the mouth and pharynx may become so numb that pulmonary aspiration may occur. Excessive absorption of benzonatate can occur if the gelcaps are chewed or allowed to dissolve in the mouth. This may lead to an overdose of the drug.

What is needed in the art are benzonatate compositions which avoid the undesirable side effects associated with release of this drug in the buccal cavity.

SUMMARY OF THE INVENTION

Modified release benzonatate solid compositions are described herein. By reducing the number of doses which are taken daily, the compositions herein provide added benefits, including convenience, for the patient. In addition, the compositions provided herein avoid release in the buccal cavity and provide a modified release of the benzonatate to reduce the number of doses required by day, thereby avoiding undesirable and potentially serious side effects associated with benzonatate. Further, the tablet is resistant to dose-dumping in the presence of alcoholic beverages. In one embodiment, the tablet has an extended release of benzonatate of about 8 to about 12 hours, when assessed in an in vitro dissolution assay, such as described herein. In certain embodiments, the dissolution assay is conducted in a USP paddle apparatus at 50 rpm at 900 mL simulated saliva, 37° C. for 20 minutes followed by a change in medium to 900 mL 0.1 N HCl at 37° C. up to 12 hours.

A modified release benzonatate tablet is provided which comprises (a) a homogenous solid dispersion comprising (i) benzonatate adsorbed onto a porous silicon dioxide to form a benzonatate adsorbate powder and (ii) a water-soluble polyethylene oxide resin in an amount effective to provide a modified release profile to the benzonatate following compression into tablet form, and (b) at least one buccoprotective coating over the homogenous solid dispersion tablet.

In a further embodiment, a modified release benzonatate tablet is provided which comprises (a) a homogenous solid dispersion comprising (i) benzonatate adsorbed onto a porous silicon dioxide to form a benzonatate adsorbate powder and (ii) a water-soluble polyethylene oxide resin in an amount effective to provide a modified release profile to the benzonatate, wherein (i) and (ii) are compressed into a tablet and form a matrix, (b) a pH-dependent, reverse enteric coat over said homogenous solid dispersion matrix tablet and (c) a non-functional coating over the reverse enteric coat. The reverse enteric coating may be (a) a pH-dependent methyl methacrylate and diethylaminoethyl methacrylate copolymer or (b) a pH-dependent cationic copolymer based on dimethylaminoethyl methacrylate, butyl methacrylate and methyl methacrylate.

In a further embodiment, a method of delivering benzonatate to a patient in need thereof is provided. The method comprises administering a modified release benzonatate tablet as described herein. In one embodiment, a single daily dose is used.

In yet a further embodiment, a method for preparing a modified release benzonatate composition is provided. This method comprises: (a) adsorbing benzonatate onto a porous silicon dioxide to form a benzonatate adsorbate powder; (b) admixing a benzonatate adsorbate powder with a water-soluble polyethylene oxide resin in an amount effective to provide a modified release profile to the benzonatate and optional excipients to form a homogenous solid dispersion; (c) compressing the homogenous solid dispersion into a tablet core; and (d) coating the tablet core with a bucco-protective coating. Optionally, the method further comprises coating the tablet core with a non-functional outer coat.

Still other advantages and aspects of the invention will be readily apparent from the following detailed description of the invention.

DETAILED DESCRIPTION OF THE INVENTION

A modified release benzonatate solid composition as provided herein is designed to avoid undesirable side effects associated with release of benzonatate in the buccal cavity, to avoid dose dumping in the presence of alcoholic beverages, and to provide improved stability in in vitro profiles. The solid compositions provided herein may be a tablet or mini-tablets loaded into a capsule.

Suitably, the tablets contain a core which is a solid homogenous dispersion comprising benzonatate adsorbed onto a porous silicon dioxide adsorbate to form a free flowing powder. The benzonatate adsorbate powder is admixed with one or more optional excipients and at least one hydrophilic polymer which forms a matrix upon compression. In a further optional embodiment, one or more active drug components may be present in the core in addition to the benzonatate. In a preferred embodiment, the hydrophilic matrix forming polymer is a water soluble polyethylene oxide resin as more fully described herein. Upon compression, the adsorbate powder, optional excipients, hydrophilic polymer, and optional additional active components form the tablet core. The tablet core is provided with a bucco-protective coat. In one embodiment, the tablet has an outer non-functional coat which does not substantially affect the release profile of the drug(s) in the tablet core. These components, and variations thereof, are described in more detail.

As used herein, a "functional coat" protects against premature release of the active drug, e.g., benzonatate, in a composition having such a coating layer over the drug. Such a functional coat may confer modified release properties to the coated drug in a time-dependent, pH-dependent, or pH-independent manner.

As used herein, a "bucco-protective coat" is a functional coat which has a time dependent release, such that a patient is protected against release of benzonatate from the tablet described herein in the buccal cavity, and suitably, also in the esophagus. In one embodiment, there is substantially no release in the first 30 minutes post-administration. However, as the tablet should pass through the buccal cavity and esophagus in less than one minute, shorter times post-administration may also be bucco-protective, e.g., 15 minutes to 30 minutes. This may be assessed in vivo and/or in an in vitro dissolution assay such as are described herein. In one embodiment, the bucco-protective coating may also function to modify release. As used herein, "modify release" involves changing the release of coated drug by more than 30 minutes, more than 1 hour, or for several hours. Typically, such "modified release" refers to changing an immediate release product to a sustained, extended, or delayed release product. Thus, in one embodiment, a bucco-protective coat also modifies the release profile of benzonatate in a tablet. Such a bucco-protective coat may contain pH-dependent (enteric or reverse-enteric) or pH-independent (barrier coat) polymers. In certain embodiments, a reverse enteric coating serves as a modified release coating, e.g., under fed conditions. In other embodiments, an enteric coating serves to slow release under fasting conditions. A tablet may contain more than one bucco-protective coat. Suitable bucco-protective coating materials are described in more detail below.

As defined herein, a "stable" in vitro and/or in vivo release profile means that the in vitro dissolution profile and/or the in vivo pharmacokinetic profile of a modified release benzonatate solid composition described herein is the same or substantially the same following storage of the composition under standard storage conditions, without requiring freezing or refrigeration, over a period of about 6 months to about 4 years. In certain embodiments, the product is shelf-stable for at least about 12 months to 4 years, at least about 18 months to 4 years, at least about 24 months to 4 years under ambient conditions compared to when assessed substantially immediately following preparation of the composition. An in vitro dissolution release profile may be assessed using a suitable assay, such as those known to those of skill in the art or described herein. For example, one in vitro dissolution assay may be conducted in USP paddle apparatus using simulated saliva as the medium. See, e.g., M.R.C. Marques, et al, "Simulated Biological Fluids with Possible Application in Dissolution Testing", Dissolution Technologies, pp. 15-28, Aug. 31, 2011 [dx.doi.org/10.14227/DT1803111P5] (see, e.g., Table 10. Simulated saliva). In one example, the USP paddle apparatus is used at 50 rpm to 75 rpm (e.g., 50 rpm) in 900 mL ±5% at 37° C.±2° C. for 20 minutes followed by a change in medium to 900 mL (+5%) 0.1 N HCl at 37° C. +2° C. up to 12 hours ±2 hours. Suitably, using the assay, compositions exhibit extended release of benzonatate of 8 to about 14 hours (or 8 to 12 hours) in 0.1 N HCl dissolution medium. An in vivo pharmacokinetic profile of the composition may be assessed using parameters known in the art including, e.g., the area under the curve (AUC), $C_{max}$, and $T_{max}$. "Substantially the same" refers to a variance of less than 5%, less than 3%, or less than 1%, between selected profile of the composition stored at controlled room temperature and the profile of the composition prior to storage for a selected time period up of at least 6 months, or at least 12 months, or more from final production. Alternatively, the assessment may be made using a shorter time period under accepted corresponding accelerated conditions (e.g., 40° C. and 75% relative humidity).

Benzonatate is characterized by the following molecular structure:

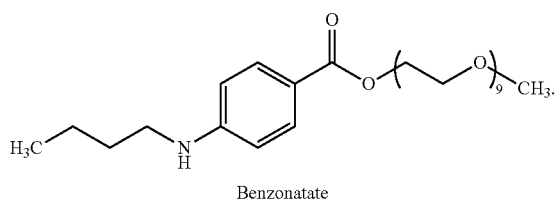

Benzonatate

The compound having the chemical name 2-[2-[2-[2-[2-[2-[2-[2-(2-methoxyethoxy) ethoxy]ethoxy] ethoxy] ethoxy] ethoxy] ethoxy] ethyl-4-butylaminobenzoate is commonly known as benzonatate. The compound has the chemical formula C30H53NO11 and a molecular weight of 603.7 g/mol (calculated based on molecular formula). Benzonatate is pale yellow oily liquid at room temperature which is water soluble and moisture sensitive, but stable. Pharmaceutical grade benzonatate is commercially available, e.g., from BASF SE and *Formosa* [Taiwan].

Optionally, the tablet may have an immediate release active component which is not benzonatate. By "immediate release", it is meant that the formulation containing the therapeutically active agent(s) meets the disintegration and/or dissolution requirements for immediate release of the particular therapeutically active agent(s), as set forth in the USP XXII, 1990 (The United States Pharmacopeia). Generally, the term "immediate release" is the release of an active ingredient from a pharmaceutical formulation where the rate of release of the active pharmaceutical ingredient from the pharmaceutical formulation is not retarded by means of a controlled release matrix or other such means and where the components of the pharmaceutical formulation are designed such that, upon ingestion, maximum exposure of said active pharmaceutical ingredient to body tissues occurs in the minimum period of time. In one embodiment for drugs other than benzonatate, immediate release provides for at least about 85% of the drug to be released in less than about one hour following administration to a patient and about 90% of the immediate release drug to be released in about 2 hours following administration to a patient. For example, a drug may release in about 10 minutes to about 45 minutes, or about 30 minutes. In another example, at least about 85%, at least about 90%, at least about 95%, or more, may be released within about 2 hours following administration to a patient.

An immediate release benzonatate composition typically provides about a 6 to 8 hour effect (e.g., Tessalon®). A modified release benzonatate such as described herein is characterized by having therapeutically effective plasma levels of benzonatate for at least about 10 to at least about 12 hours following administration and up to about 24 hours. Thus, the formulation described herein advantageously provides for less dosing frequency as compared to an immediate release formulation (e.g., 1-2 doses eliminated in a 24 hour period).

The compositions described herein help to avoid an undesirable side effect associated with release of benzonatate in the buccal cavity or esophagus which side effects include temporary, potentially life-threatening local anesthesia of the oral mucosa, choking, or severe hypersensitivity reactions; oropharyngeal anesthesia can develop rapidly with improper administration. As used herein, the phrase "substantially no release of benzonatate" in the buccal cavity means that no amount of benzonatate and/or no amount of benzonatate which causes these side effects is released buccal cavity. As used herein, the term "buccal cavity" refers to the mouth, i.e., the area bounded by the lips, cheeks, and tongue.

A modified release solid composition comprising benzonatate is provided. In one embodiment, the composition provides a 12-hour tablet or capsule (e.g., mini-tablets in a capsule) with a pharmacokinetic profile for benzonatate which has $AUC_{inf}$ of about 196 ng-h/mL to about 307 ng-h/mL, or values therebetween such as 200 ng-h/mL to 275 ng-h/mL, or about 245 ng-h/mL to 150 ng-h/mL, a geometric mean $C_{max}$ of about 26 ng/mL to about 42 ng/mL, or about 33 ng/mL, and a $T_{max}$ of about 3 to 5 hours, or about 4 hours, following a single dose equivalent to about 300 mg benzonatate in adults under fasting conditions. In certain embodiments, a daily dose is 600 mg, e.g., administered at the equivalent of 300 mg benzonatate per dose at about 12 hour intervals (two times per day). In certain embodiments, the composition provides a 12-hour tablet or capsule with a pharmacokinetic profile for benzonatate in which its $AUC_{inf}$ of about 154 ng-h/mL to about 242 ng-h/mL, or values therebetween such as 175 ng-h/mL to 200 ng-h/mL, or about 193 ng-h/mL, a $C_{max}$ of about 28 ng/mL to about 44 ng/mL, or about 35 ng/mL, and a $T_{max}$ of about 6.4 to 10 hours, or about 8 hours following a dose equivalent to 300 mg benzonatate in adults under fed conditions. In certain embodiments, a daily dose is 600 mg, e.g., administered at the equivalent of about 300 mg benzonatate at about 12 hour intervals (two times per day).

In certain embodiments, a composition provided herein is characterized by having a pharmacokinetic profile provided by a composition is characterized by a single plasma concentration peak following each dose.

In another embodiment, a composition is provided which is characterized by one or more of the following in vivo pharmacokinetic parameters when determined by arithmetic mean: $C_{max}$ (ng/mL) of about 30.5 ng/mL to about 38 ng/mL: $AUC_{inf}$ (ng·h/mL) of about 220.5 to about 238.5 ng/mL, $T_{max}$ (h) of about 3 h to 16.5 h (median). In a further embodiment, the composition is characterized by one or more of the following in vivo pharmacokinetic parameters when determined by geometric mean: $C_{max}$ (ng/mL) of about 29.5 ng/mL to about 36 ng/mL: $AUC_{inf}$ (ng·h/mL) of about 190.5 to about 232 ng/mL, $T_{max}$ (h) of about 0.5 to about 17 h (median). In certain embodiments, the pharmacokinetics are determined following a dose equivalent to about 300 mg benzonatate in adults under fasted conditions. In certain embodiments, a daily dose is about 600 mg, e.g., administered at the equivalent of about 300 mg benzonatate, at about 12 hour intervals (e.g., up to two times per day). In certain embodiments, the pharmacokinetic profile for benzonatate provided by the composition of the invention is characterized by a single plasma concentration peak following a single dose.

As used herein, the term $C_{max}$ refers to the maximum (or peak) serum concentration that a drug achieves after the drug has been administered and prior to the administration of a second dose. In certain embodiments, $C_{max}$ may be determined using arithmetic mean. Unless otherwise specified, the $C_{max}$ values provided herein are geometric mean values.

The term "area under the curve $(AUC)_{inf}$" refers to the total drug exposure over time (extrapolated to infinity)

starting at the time the drug is administered and extrapolated to infinity. The word portion "inf" may be used interchangeably with the infinity symbol: "∞". The $AUC_\infty$ ($AUC_{inf}$) may be calculated as an arithmetic mean or geometric mean of drug concentration measured at certain time points post-dosing. Typically, a calculation method accepted by an appropriate drug/market regulatory approval agency for the selected territory will be selected. For example, if arithmetic mean is selected, the values may be calculated as the sum of the numbers (used to produce the AUC curve) divided by the number of numbers in the collection. In another example, if geometric mean is selected, it may be calculated as the mean of the area under the plasma concentration-time curve from time zero extrapolated to infinity, calculated for each individual participating in the bioavailability study. In general, for geometric mean, the drug concentration is measured at certain discrete points in time and the linear trapezoidal rule is used to estimate AUC.

"Bioequivalence" refers to the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. In certain circumstances, pharmacokinetic profile of a test composition is within the range of about 80% to about 125% at a 90% confidence interval, or in certain embodiments, a 95% confidence interval, when compared to the values of at least one of the $AUC_{0-inf}$, $AUC_{0-t}$, or the $C_{max}$ of the reference composition under fasted conditions. This may be based upon geometric or arithmetic mean and calculated as accepted by a suitable regulatory agency. Optionally, there may also be bioequivalence under fed conditions. In certain embodiments, if a food effect is observed, the product may be labelled "not to be taken with food".

"Confidence interval" (CI) is calculated using nonparametric percentile bootstrap confidence interval procedure (upper bound of the 90% two-sided confidence interval) using a minimum of 1500 (2000 recommended) bootstrap samples that preserve the number of subjects per sequence. See, e.g., Guidance for Industry, Statistical Approaches to Establishing Bioequivalence, US Department of Health and Human Services, Food and Drug Administration, Center for Drug Evaluation and Research (January 2001). Alternatively, another suitable calculation method acceptable to an appropriate regulatory agency may be selected. See, also, B. Larget, Chapter 3 R Bootstrap Examples, Feb. 19, 2014, www.stat.wisc.edu.

As used herein, the term "equivalent" to free benzonatate or another drug (e.g., guaifenesin) base is used to refer to the weight of the base (or acid) portion of the compound without the counterion, or the free drug portion of a drug—ion exchange resin complex, without taking into account the weight of the cation exchange resin or any matrix or coating component.

"$C_{max}$" is the peak drug concentration. In certain embodiments, this is the maximum observed plasma concentration, calculated as the mean of the individual maximum blood plasma concentrations. This may be calculated using the geometric or arithmetic mean as described above.

The term "$T_{max}$" is the time at which the peak (maximum) observed blood plasma drug concentration for each patient as determined following a single dose. The $T_{max}$ may be determined based on the geometric curve or arithmetically.

As used herein, "mini-tablets" are tablets with a diameter ≤3 mm produced on conventional tablet presses. Suitable equipment is commercially available (e.g., KG Pharma). Such mini-tablets may be loaded into a capsule to provide a solid oral dosage form. Typically, a capsule with contain multi mini-tablets in a single capsule, in order to provide the desired dose. For example, a capsule may contain two to six, or more mini-tablets, more commonly three, four or five mini-tablets. Pharmaceutically acceptable empty soft and hard capsules are commercially available from a variety of sources. Suitable capsules are available, and suitable sizes include "000", "00", "0", 1, 2, 3, 4 or 5. See, Capsulon, Capsuline, or another company. For example, a 150 mg dose may contain 5 mini-tablets in a single capsule of size "0". However, other size capsules and other numbers of mini-tablets may be selected. Similarly, a gelatin capsule may be selected, or a vegetarian capsule. However, other pharmaceutical grade capsule shells may be selected.

The words "comprise", "comprises", and "comprising", and "containing" and it variants are to be interpreted inclusively rather than exclusively, i.e., allow other components. The works "consist", "consisting", and its variants, are to be interpreted exclusively, rather than inclusively.

As used herein in reference to numeric values provided herein, the term "about" may indicate a variability of as much as 10% (up to f 10% of the indicated value, including). This includes lower variabilities (e.g., ±1%, ±2%, ±3%, 4%, ±5%, ±6%, ±7%, ±8%, ±9%, and other values between 0 and 10).

Benzonatate Adsorbate

As used herein, the term "adsorbent" refers to a substance or carrier capable of converting liquid benzonatate into a dry, non-adherent, free-flowing compressible powder. The term "benzonatate adsorbate" refers to the compressible powder formed when benzonatate is adsorbed onto an adsorbent. A powder is free flowing if it meets the processing characteristics such that in the process of making tablets the resulting tablet weights are uniform. Further, a powder is considered compressible if the resulting tablet with the hardness that can sustain <1% friability using USP test method.

As provided herein, porous silicon dioxide having these free flowing and compressibility characteristics is selected as the adsorbate. One particularly desirable characteristics of silicon dioxide powder is a high internal surface area, meaning that the porous silicon dioxide has an average surface area of about 300 m$^2$/g to about 1000 m$^2$/g, 300 m$^2$/g to about 750 m$^2$/g, or about 320 m$^2$/g. The surface area of the porous carrier may be measured using standard procedures. One exemplary method is by low-temperature nitrogen adsorption, based on the Brunauer, Emmett and Teller (BET) method, well known in the art [see, K. Sing et al, Colloids and Surfaces, A: Physiochemical and Engineering Aspects 187-188 (2001), 3-9); see also, BET Method at BS 4359-1:1996 (International Organization for Standards (ISO) 9277:1), Geneva Switzerland; and http://particle.dk/methods-analytical-laboratory/surface-area-bet/surface-area-bet-theory/]. In certain embodiments, the porous silicon dioxide has an average bulk density of about 150 g/L to about 350 g/L, or about 210 g/L to 275 g/L (a weighed solid is introduced into a measuring cylinder. The volume occupied by the solid is measured. Bulk density=Weight/Volume). In certain embodiments, the porous silicon dioxide has an oil absorption capacity of about 1 parts by weight benzonatate to 1 part by weight silica to about 5 parts benzonatate to about 1 part by weight silica, 3 parts by weight benzonatate to about 1 part by weight silica (or about 300 lbs benzonatate to 100 lbs silica). In certain embodiments, the porous silicon dioxide has a minimum pore volume of 1.5 cc/gm to 2 cc/gm, or at least 1.7 cc/gm.

Typically, pore volume is calculated by mercury (Hg) intrusion/extrusion technique. See, e.g., Syloid® XDP Silica, Silica-Based Carrier with Extra Density and Porosity, Grace White Paper. Suitable commercial products are available, e.g., from Grace, as Syloid® XDP 3150, and Syloid® 350 XDP, both of which have typical surface areas of 320 m²/g. The Syloid® XDP 3150 has an average particle size (measured via the Malvern method) of 120 m to 170 m, or about 150 µm, an oil adsorption capacity of 300 lbs benzonatate/100 lbs silica, a bulk density of 275 g/L, an average pore volume of at least 1.7 cc/gm. [See, e.g., Basic Principles of Particle Size Analysis, by Dr. Alan Rawle, Malvern Instruments Limited, pp. 1-8; see, e.g., ISO 13320 (2009) which covers the laser diffraction technique for measuring particle size distributions from nanometers to millimeters]. Suitably, this porous silicon dioxide powder provides several advantages, including good flow, improved product uniformity, and it substantially reduces or eliminates "weeping-out" of the benzonatate liquid during the manufacturing processes such as tablet compression. However, in certain embodiments, other silicas, silicates, less porous silicon dioxides, or other porous metallic dioxides may be used to form benzonatate adsorbates which may be blended with the benzonatate—porous silicon dioxide adsorbate described herein.

In general, benzonatate is admixed (granulated) with one or more adsorbent materials as described herein to form a benzonatate adsorbate. For admixing, the benzonatate to adsorbent ratio is generally a ratio of about 5:1 to about 1:2, or about 4:1 to about 1:1, or about 3:1 to about 2:1, or about 2:1 to about 1:1. In one example, the ratio is about 1:0.6. In one embodiment, the benzonatate adsorbate comprises about 10% w/w to about 80% w/w benzonatate, about 20% w/w to about 70% w/w, about 50% w/w to about 70% w/w, about 50%, or about 25% to about 30% w/w benzonatate adsorbate.

In order to facilitate production and even distribution of the adsorbate in the hydrophilic matrix, the benzonatate adsorbate powder granules are typically passed through a screen of about 425 microns, which allows granules or particles having an average size of less than about 420 µm to pass through. In certain embodiments, the particles are in the size range of the porous silicon dioxide having the high internal porosity. The particles may be in the size range of about 50 µm to about 250 µm, or about 75 µm to about 150 µm.

The benzonatate adsorbate may be admixed with any tableting excipients or other components (e.g., a pharmaceutically active ingredient in addition to benzonatate) prior to being mixed with the matrix-forming substance. Alternatively, the benzonatate adsorbate and the matrix-forming substance, as well as one or more excipients, and/or or an additional pharmaceutically active component, are combined at substantially the same time. Thus, the tablet core may comprise excipients and optional additional pharmaceutically active component. Still other production techniques may be designed by one of skill in the art in view of the information provided herein.

Tablet Core

To form the tablet core, at a minimum, the benzonatate adsorbate powder is admixed with a hydrophilic matrix forming polymer which is selected to control (modify) the rate of release of benzonatate and any other optional active components in the core. In one particularly desired embodiment, polyethylene oxide water-soluble resins as defined herein are particularly well suited for use as a rate-controlling polymer for the benzonatate adsorbate.

Other methods, including light scattering and gel permeation chromatography, may not be directly comparable. Such other methods of measuring molecular weight are known and include, e.g., weight-average molecular weight, number-average molecular weight, and polydispersity can be determined by aqueous size-exclusion chromatography with a multiangle laser light-scattering (SEC-MALLS) detector. The SEC system consists of a pump (Waters 2690 pump, Milford, MPA), connected with a DAWN (MALLS) detector (Wyatt Technology, Santa Barbara, CA) and a Wyatt differential refractive Polyethylene oxide is a nonionic homopolymer of ethylene oxide. In certain embodiments, polyethylene oxide resins having a molecular weight in the range of about 600,000 to about 5,000,000 (as determined using rheological methods), or values therebetween, e.g., about 750,000 to 4,000,000, or about 800,000 to about 2,000,000, or about 850,000 to about 1,500,000. In general, a lower molecular weight polyethylene oxide will provide a faster release to the benzonatate and a higher molecular weight polyethylene oxide will provide a slower release to the benzonatate. See, e.g., H Zhang, "Rheological Method for Determining Molecular Weight and Molecular Weight Distribution, www.intechopen.com, Materials Science and Technology, pp. 313-324 (March 2012)]. Molecular weights obtained by index detector. The SEC fractionation of analyzed sample is evaluated to ensure an ideal SEC separation.

In certain embodiments, the polyethylene oxide that is selected has a viscosity in the range of about 7500 to about 20,000 (as determined in a Brookfield Viscometer), or values therebetween, e.g., 8,800 cP to 17,600 cP at 25° C. (5% solution). Viscosity determinations for PEO samples are made using a digital viscometer (Brookfield DV-II+ viscometer, Brookfield Engineering Laboratories, Middleboro, MA), 5% aqueous solution, with spindle 2 at 2 rpm. The working examples below illustrate use of a polyethylene oxide available under the trade name Polyox™ from Dow Chemical Company. Various water soluble grades of Polyox™ are available that differ in terms of molecular weight and viscosity range. To illustrate, the examples below describe the use of Polyox™ WSR-1105, which has an approximate molecular weight of 900,000 (based on rheological measurements) and a viscosity range of 8,800 cP to 17,600 cP at 25° C. (5% solution) assessed in Brookfield Viscometer, Model RVF, Spindle No. 2/rpm 2.

Suitably, the selected polyethylene oxide water-soluble resins comply with The National Formulary Standard for "polyethylene oxide" in USP 23-NF 18 issued in 1995, and in subsequent formularies. Polyethylene oxide has the following advantages: It is a thermoplastic material and imparts good hardness to the tablets without the requirement of other tablet compression aid excipients. There is also no drop or increase in hardness during stressed stability studies, thus no change in the dissolution profiles.

Optionally, another "pH-independent, low viscosity, matrix-forming, modified release hydrophilic polymers" may be combined with the polyethylene oxide water soluble resin as defined above. As used herein, the "pH-independent, low viscosity, matrix-forming, modified release hydrophilic polymers" includes hydrophilic polymers which have a viscosity of less than 1000 eps, which are solids at room temperature and which, when compressed into a matrix afford modified release properties to a drug within the matrix which is so formed. Suitable polymers may include natural gums, such as acacia gum tragacanth, gum arabic, locust bean gum, guar gum, karaya gum, tamarind gum, xanthan gum, amylose, arabinans, cellulose, galactomannans, gum karaya, tragacanth, gellan gum, agar, algin, carrageenan, pectic acid, alginic acid, laminarin, gum ghatti, khaya gum and *albizia* gums, larch gum, chitin and chitosan, chondroitin sulfate, hyaluronic acid, dextran, curdian, pullulan, zanflo, emulsan, Baker's yeast glycan, agarose, collagen, fibrin, hyaluronic acid, schizophyllan, lentinan, scleroglucan, modified celluloses, including methylcellulose, hydroxymethylcellulose (HMC), hydroxypropyl cellulose (HPC), hydroxyethylcellulose, carboxymethylcellulose, hydroxypropyl methylcellulose (hypromellose or HPMC), agar, pectin, carrageenan, alginate, carboxypolymethylene, gelatin, casein, and modified starch derivatives, or combinations thereof.

A variety of food grade and pharmaceutical grade hydrophilic polymers are commercially available. For example, METHOCEL™ K-type Food Grade HPMCs, including, e.g., K100M, K15M, F4M, K4M, K100LV, K3, E15LV, E5 and E3. For purposes of illustration only, these may have average viscosities of about 4000 mPa-s (K4M), about 15,000 mPa-s (K15M), or about 100,000 mPa-S. One hydroxypropyl cellulose [LXF, Ashland Chemical] is characterized by a molecular weight of 95,000 and a viscosity of 75-150 mPa-S. Another illustrative HPC is characterized by a viscosity of 300 to 600 mPa-s and a molecular weight of about 80 kDa. Combinations of hydrophilic polymers may be utilized, including a combination of two or more hydrophilic polymers within the same class, but having different viscosities or molecular weights (e.g., two HPMCs), or two or more hydrophilic polymers of different classes (e.g., an HPC and an HPMC).

Thus, as described herein, a benzonatate adsorbate powder is admixed with the polyethylene oxide (and, if desired, another hydrophilic polymer as defined herein) and/or other excipients or active components to form a tablet core. The water soluble polymer is used in a concentration of about 10% to 90% w/w, more preferably 15% to 55% w/w, 20% to 40% w/w, 25% to 35% w/w, or about 30% w/w, based on the weight of the polymer/copolymer/blend to total weight of the tablet core. In certain embodiments, the weight ratio of benzonatate adsorbate to polyethylene oxide is about 2:1 to about 1:3 (about 2 parts benzonatate adsorbate to about 3 parts polyethylene oxide to about 1 part benzonatate adsorbate to about 3 parts polyethylene oxide, or about 1.5 part benzonatate adsorbate to about 1 part polyethylene oxide. The polymer is present in sufficient amount to provide the desired benzonatate release.

As used herein, the term "tablet core" refers to the formed tablet with active component and excipients prior to application of any coating.

In order to facilitate processing, the selected polyethylene oxide may be passed through a screen of about 600 microns prior to admixing with the benzonatate adsorbate powder. As previously discussed, the benzonatate powder may be passed through a 425 micron screen. Other excipients which are present in the tablet core, e.g., bulking agents, fillers, and the like, may also be passed through a similarly sized 425 micron screen. Optionally, certain excipients, e.g., a lubricant, may be passed through a smaller screen (e.g., a 150 micron to 425 micron, or a 250 micron screen).

Typically, a benzonatate composition as provided herein may contain a filler or a mixture of fillers in the range of about 10% w/w to about 50% w/w, about 20% w/w to about 40% w/w, or about 30% w/w of the total tablet or capsule weight. As used herein, the term "filler" and "bulking agent" are used interchangeably. Suitable fillers may include, e.g., mannitol, lactose, maltose, fructose, sucrose, xylitol, maltitol, microcrystalline cellulose, dicalcium phosphate, guar gum, xantham gum, tragacanth gum, pre-gelatinized starch, compressible sugar, calcium carbonate, magnesium carbonate, calcium sulfate, dextrates, maltodextrin. In one embodiment, a benzonatate tablet contains a blend of microcrystalline cellulose and lactose monohydrate. In certain embodiments, the bulking agent is selected from isomalt or microcrystalline cellulose, hypromellose, or another cellulose derivative, or combinations thereof. However, other suitable bulking agents are known and may be selected. The bulking agent may be present in the core in an amount of about 20% by weight to about 50% by weight. In certain embodiments, the binder is copovidone. Such binder(s) are generally present in an amount of about 30% to about 50% by weight of the tablet core.

The binder for a composition as provided herein may be absent (i.e., 0%), or optionally, present in an amount of about 1% w/w to about 15% w/w of the total tablet weight. Examples of suitable binders include polyvinylpyrrolidone (povidone), hydroxypropyl methyl cellulose, hydroxypropyl cellulose, hydroxyethyl cellulose, methyl cellulose, polyvinyl alcohol, starch, acacia, alginic acid, sodium alginate.

In order to facilitate production of a benzonatate composition as provided herein, excipients such as lubricants and glidants may be utilized. A lubricant may be utilized in an amount of about 0.1% w/w to about 5% w/w, about 0.2% w/w to about 4.5% w/w, or about 1.5% w/w to about 3% w/w of the total weight of the tablet. Examples of lubricants may include, e.g., talc, magnesium stearate, sodium stearyl fumarate, stearic acid, zinc stearate, calcium stearate, magnesium trisilicate, polyethylene glycol, and blends thereof. Examples of suitable glidants include, e.g., silicon dioxide, magnesium stearate, calcium stearate, and tribasic calcium phosphate, vegetable oils, polyethylene glycols, talc, sodium lauryl sulfate, polyoxy ethylene monostearate, and mixtures thereof. In one embodiment, the glidant is silicon dioxide which is used in an amount of about 0.001% w/w to about 0.1% w/w or about 0.05% w/w.

Optionally, other excipients may be selected from conventional pharmaceutically acceptable carriers or excipients and well established techniques. Without being limited thereto, such conventional carriers or excipients include diluents, binders and adhesives (i.e., cellulose derivatives and acrylic derivatives), disintegrants, flavorings, stabilizing agents, sweeteners, and miscellaneous materials such as buffers and adsorbents in order to prepare a particular pharmaceutical composition. The stabilizing agents may include preservatives and anti-oxidants, amongst other components which will be readily apparent to one of ordinary skill in the art.

Optionally, a colorant may be provided to the tablet to provide a desired visual appeal or trade dress. Such colorants may be added in the range of about 0.001% w/w to about 1% w/w, or about 0.01% w/w to about 0.08% w/w or about 0.05% w/w, based on the total weight of the tablet (exclusive of any bucco-protective coating). Such colorants are available from a variety of commercial sources including, e.g., Colorcon, Noveon, and Spectra. Alternatively, such colorants may be provided in the non-functional outer coating and/or the bucco-protective coating described in this specification.

In general, the benzonatate adsorbate described herein is about 25% to about 50%, by weight, of the tablet core. The remaining components of the tablet core include optional active ingredients and one or more excipients which are non-reactive with benzonatate and the other components of the tablet core.

In addition to the compositions described herein where benzonatate is the single active ingredient, benzonatate composition may further comprise one or more pharmaceutically active components. Each of these additional active drugs may be independently in modified release form and/or immediate release. For example, a modified release drug may be blended into the tablet core; whereas an immediate release drug may be applied as a layer on the tablet core. In another embodiment, a modified release drug may be layered onto the tablet core. Still other alternatives will be apparent to one of skill in the art.

Particularly suitable classes of pharmaceutically active drugs for combination with the benzonatate include an anti-pyretic, an analgesic, an anti-histamine, an expectorant and a decongestant. Examples of suitable antipyretic analgesics include, e.g., sodium salicylate and salicyclic acid, non-steroidal anti-inflammatory drugs (NSAID), including ibuprofen, naproxen, aspirin, magnesium salicylate, diclofenac, etodolac, indomethacin, nabumetone, sulindac, tolmetin, ketoprofen, mefenamic acid, meclofenamic acid, phenylbutazone, piroxicam, meloxicam, celecoxib, parecoxib, rofecoxib, valdecoxib, and salts thereof. Examples of opioid analgesics drugs such as alfentanil, allylprodine, alphaprodine, anileridine, benzylmorphine, bezitramide, buprenorphine, butorphanol, clonitazene, codeine, cyclazocine, desmorphine, dextromoramide, dexozine, diampromide, dihydrocodeine, dihydromorphine, dimenoxadol, dimepheptanol, dimethylthiambutene, dioxaphenylbutyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, morphine sulfate, myrophine, nalbuphine, narceine, nicomorphine, norlevorphanol, normethadonel, nalorphine, normorphine, norpipanone, opium, oxycodone, oxymorphone, papaveretum, pentazocine, phenadoxone, phenmorphan, phenazocine, phenoperidine, piminodine, piritramide, proheptazine, promedol, properidine, propiram, propoxyphene, sufentanil, tramadol, tiline, salts thereof, mixtures of any of the foregoing, mixed mu-agonists/antagonists, mu-antagonist combinations. Examples of suitable antihistamines include both sedating and non-sedating antihistamines, e.g., fexofenadine HCl— or dl-chlorpheniramine maleate, diphenhydramine, loratadine, desloratadine, meclizine, pheniramine, cetirizine, and promethazine. Examples of antitussive expectorants include, e.g., such as guaifenesin, dihydrocodeine phosphate, codeine phosphate, noscapine hydrochloride, phenylpropanolamine hydrochloride, potassium guaiacolsulfonate, cloperastine fendizoate, dextromethorphan hydrobromide and cloperastine hydrochloride. Examples of bronchodilators include, e.g., dl-methylephedrine hydrochloride and dl-methylephedrine saccharinate. Examples of decongestants include, e.g., pseudoephedrine hydrochloride, phenylephrine bitartrate, and pseudoephedrine sulfate.

One suitable combination includes guaifenesin.

As described herein, a tablet core is prepared by admixing the benzonatate adsorbate powder and a suitable polyethylene oxide with other selected core components and compressing the admixture. In order to have the powder in the free-flowing form, granulation processes are employed. The powder can be compacted using suitable equipment followed by milling into suitable size granules. The granules are further lubricated and compressed into tablets. Dry granulation is a process of compression of powders by either slugging or roller compaction. It is essentially a densification process. In slugging a crude compact (slug) is produced and subsequently these slugs are then reduced by either grating or commuting mill to produce granules of the required particle size/range. Roller compaction or chilsonation is a process in which a powder mix is forced via an auger between 2 rollers to get powder compacts. The resulting compacts (referred as ribbon or strip) are then size-reduced by either grating or commuting mill to produce granules of the required particle size/range. In the wet granulation method, the active is mixed with the excipients followed by addition of a suitable liquid binder in order to granulate the powder. Various mixer designs are available, for example: wet high shear mixers (rotating high shear forces), low shear mixers (planetary mixer), wet low shear tumble, (spraying in to tumble mixer with/without intensifier bar), extrusion, (wet solid is forced through screen), rotary granulators (spheronization or marumerization), spray granulation in a fluidized bed systems, spray dry granulation etc. The resultant granules are dried, lubricated and compressed into tablets using a suitable tablet compression machine.

In one embodiment, the tablet has a hardness of about 5 kilopond (kp) to about 25 kp, about 8 to about 20 kp, or 10 to about 15 kp. In certain embodiments, the mini-tablet has a hardness in the range of about 2 kp to about 4 kp. One (1) kilopond is one kilogram of force (kgf). Newtons (N) are the SI unit of force and the SI standard for tablet hardness testing. 1 kilopond (kp) is equal to 9.80665 Newtons (N). Presented in Newton rounded to the nearest five, the tablet has a hardness of about 45 N to about 245 N, about 75 N to about 200 N, or about 95 N to about 160 N. Optionally, the hardness may be dose proportional, with lower doses having lower hardness levels. For example, a 20 mg tablet may have a hardness in the range of about 10 to about 12 kp (about 98 N to about 118 N), a 30 mg tablet may have a hardness in the range of about 12 to about 14 kp (about 118 N to about 137 N), and a 40 mg tablet may have a hardness in the range of about 14 kp to about 16 kp (about 137 N to about 156 N). In one embodiment, the hardness is determined following compression and prior to application of any color or other bucco-protective tablet coating as defined herein. In one embodiment, the tablets meet the USP Friability requirement. In one embodiment, the friability of both the intact tablet and the tablet portions are less than about 1. See, e.g., USP35, General Information/(1216) Tablet Friability, p. 867-868, US Pharmacopeia (Dec. 1, 2012).

Coating of Tablet Core

The tablet contains, at a minimum, at least one, independently selected, bucco-protective coating over the core. As described herein, the bucco-protective coating has a time-dependent drug release profile.

In one embodiment, a bucco-protective coating layer may include a polymer or non-polymeric components. Examples of suitable bucco-protective components include, e.g., without limitation, prolamine (Zein); hypromellose (a single grade or a mix of different viscosity grades; see, e.g., Opadry® TM brand from Colorcon; modified pea starch (e.g., ReadiLycoat® by Roquette; shellac (e.g., Certiseal® FC-300 from Mantrose); a mixture of hypromellose and fats (e.g., Aquapolish® D from Biogrund); a mix of cellulose and wax (e.g., carnauba wax/bees wax etc.; one suitable product is Aquarius® MG from Ashland), a hot melt coating blend comprising one or more of precirol, sterotex, beeswax, or cetyl alcohol, a sodium alginate and/or calcium alginate, or mixtures thereof, optionally with a solvent and/or other coating components. As described herein, a "high molecular weight" hydromellose (hydroxypropylmethylcellulose, HPMC, is characterized by having a viscosity in the range of about 10,000 cP to about 100,000 cP). The above coating materials could be used alone or in combinations thereof. In general, a bucco-protective coat is present in an amount of about 10% by weight to about 50% by weight, of the total tablet weight.

In one embodiment, a bucco-protective coating layer may include a pH-dependent (enteric coat or reverse enteric) coat or a pH-independent barrier coat. In one embodiment, an enteric coat may be selected. An enteric coat is pH-dependent and is designed so that it dos not swell or become permeable at the low acid environment of the stomach, e.g., pH 2 to 4, about pH 3, and to release in higher (e.g., pH 4.5 and above), neutral (e.g., pH 6 to 8) or alkaline pH (e.g., pH 8 to 9 or above). This coating is designed to provide for drug release in the intestine which has a higher pH than the stomach. A variety of enteric coating materials and products are known. Examples include, e.g., cellulose acetate phthalate, polyvinylacetate phthalate, hydroxypropyl methylcellulose phthalate, and pH-dependent acrylate polymers and co-polymers, some of which are commercially available in the Eudragit® product line by Evonik Industries (e.g., the Eu® L series (L30 D-55 or L100-55 (dissolution above pH 5.5), L100 or L12,5 (dissolution above pH 6.0)), or the S series (S100, S12,5, FS 30D (dissolution above pH 7.0)).

In another embodiment, a reverse enteric coating may be used in a benzonatate tablet as provided herein. In contrast to an enteric coating which is designed to avoid dissolution in the acidic pH of the stomach, a reverse enteric coating is designed to solubilize or swell in the presence of low acid environments (e.g., less than about pH 4, or less than about pH 3.5, or less than about pH 3). A reverse enteric coating is pH-dependent and designed not to solubilize or swell in pH greater than about pH 4, or greater than about 4.5. One suitable reverse enteric polymer is an acrylate polymer or copolymer. Particularly suitable reverse enteric coats include those polymers which can be applied as aqueous dispersions. One suitable aqueous dispersion is based on methyl methacrylate and diethylaminoethyl methacrylate copolymer. One example of such a reverse enteric coat is Kollicoat® Smartseal 30D, which is an aqueous polymeric dispersion with a solids concentration of approximately 30%. It contains methyl methacrylate and diethylaminoethyl methacrylate copolymer stabilized with approximately 0.6% macrogel cetostearyl ether and 0.8% sodium lauryl sulfate. Still other reverse enteric polymers include, e.g., Eudragit® E 100 (Evonik), Eudragit® E PO (Evonik), methyl methacrylate, hydroxyl ethyl methacrylate and a random terpolymer based on methyl methacrylate, 2-hydroxy ethyl methacrylate and 4-vinylpyridine. The Eudragit® E PO is Poly (butyl methacrylate-co-(2-dimethylaminoethyl) methacrylate-co-methyl methacrylate) 1:2:1 (CAS number: 24938-16-7), i.e., a cationic copolymer based on dimethylaminoethyl methacrylate, butyl methacrylate and methyl methacrylate having an average molecular mass of about 47,000 g/mL, an alkali value of 180 mg KOH/g polymer, and a glass transition temperature of 45° C. (±5° C.) having the structure:

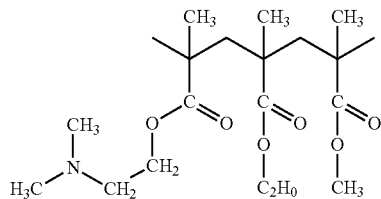

The commercial Eudragit® E PO Ready Mix consists of basic butylated methacrylate copolymer, sodium lauryl sulphate, stearic acid and talc. However, other surfactants, including other anionic surfactants, may be substituted for sodium lauryl sulfate in other formulations. Examples of suitable surfactants other than the anionic surfactant sodium lauryl sulfate are known to the skilled artisan. Similarly, lubricants other than stearic acid and glidants other than talc are known in the art and may be selected. Still other reverse enteric polymers are described, and may be made, as described, e.g., US 2006/062844 (2006); US 2005/0136114, U.S. Pat. No. 7,294,347, the disclosure of which is incorporated herein by reference.

Weight percentages of reverse enteric coatings, when present, are provided as weight added, in an amount of about 5% to about 60%, or about 5% to about 20%, or about 8 to about 12% weight added to the finished tablet.

In another embodiment, a bucco-protective coat has both time dependent release function and a pH-independent, modified release, barrier coat function. As used herein, a "barrier coating" refers to a pH-independent coating which alters the release profile of a barrier-coated drug. A variety of different modified release barrier coatings have been described and/or are commercially available. Examples include, without limitation, coating containing polymers and/or copolymers containing one or more of the following: ethylcellulose (see, e.g., ethylcellulose brands Surelease® by Colorcon, Ethocel® by Dow Chemical, Aqualon® by Ashland) and acrylate polymers and copolymers (see, e.g., the Eudragit® RS and RL series), a blend comprising ethyl acrylate and methylmethyacrylate copolymer and a sodium carboxymethylcellulose; a blend of ethylcellulose and a hydrophilic polymer; a blend of polyvinylacetate and a hydrophilic polymer (e.g., polyvinylpyrrolidone), a polyvinyl alcohol and polyethylene glycol graft copolymer; a methylmethacrylate and diethylaminoethyl methacrylate copolymer, or mixtures thereof, optionally with a solvent and/or other coating components. In one embodiment, the non-aqueous solvent-based ethylcellulose [such as in commercially available as the line of ETHOCEL™ products by Dow] is used. Dow's web site describes three of these products, Std 7 (viscosity of 6-8 mPa-s (CP); Std 10 (9-11 mPa-s (CP); Std 20 (18-22 mPa-S), each of which has a 48.0-49.5% ethoxyl content) as being useful for tablet coating. Further, optionally combining one of these polymers in combination with a water-soluble active and/or water-soluble excipient such as a METHOCEL™ cellulose ether and/or CARBOWAX™ polyethylene glycols is further described. Optionally, such a coating may be modified in order to achieve the preferred release profile characteristics defined herein, e.g., by inclusion of a sufficient amount of plasticizer to improve flexibility and/or by curing to a sufficient temperature to achieve the desired release rate from the coating.

Additionally, a tablet may contain a non-functional outer coating which does not confer any modified release properties on a coated drug. The non-functional coating may contain a polymer, or a non-polymeric material, which is a moisture barrier to preserve the integrity of the tablet during storage or to facilitate application of a color coating layer and may alternatively be referred to herein. Examples of non-functional outer coating materials may comprise one or more components which provide moisture barrier (sealant) and/or oxygen barrier and/or color and/or smoothness. As provided herein, some of these products are available commercially. See, e.g., a low molecular hypromellose, methylhydroxy ethylcellulose, hydroxypropyl cellulose, polyvinyl pyrrolidone, polyvinyl alcohol (see, e.g., Opadry® II (polyvinyl alcohol, polyethylene glycol, talc), sodium carboxymethyl cellulose; a combination of polyacrylic resin, carbomer, and a powdered cellulose coat. As used herein, a "low molecular weight" has a viscosity of about 100 cP to about 5000 cP. In one embodiment, the non-functional coating may increase the hardness of the tablet. Weight percentages of these non-functional coatings, where present, are provided as weight added, in an amount of about 1% to about 20%, or about 2% to about 10%, or about 3% to about 5% weight added to the finished tablet.

The tablet may be loaded into a capsule alone, or manufactured as mini-tablets which are loaded into a capsule shell. Alternatively, the power may be loaded into a capsule which capsule shell is provided with a functional coating. In one embodiment, the coating may be a reverse enteric coating.

Optionally, a tablet may have an outer coating which has a single layer which is a blend of a bucco-protective coating and a second functional coating. The above bucco-protective, barrier coating, and reverse enteric coating materials could be used alone or in combinations thereof. Certain "modified release" coatings may be used as a bucco-protective coating; in such instances, these polymers, copolymers or blends are used in thicknesses (weights) in an amount of about 1% to 5% by weight, based on the total weight of the uncoated tablet. A coating as described herein may be applied using techniques described by the polymer manufacturer and/or techniques which are known to those of skill in the art. Suitable methods and apparatus have been described in the patent and non-patent literature and include, e.g., spraying in a fluid bed processor. Spraying the coating solution in a fluid bed processor (e.g., VECTOR™ FLM-1 fluid bed processor) using Wurster process. The coated tablets can then be dried.

Finished Compositions Dosage Forms

A benzonatate composition as described herein may be a compressed tablet core provided with a bucco-protective coating, optionally with an intermediate layer which is a pH-dependent coating. Compressed tablets may be mini-tablets which are loaded into capsule shells or designed to be of a size for direct administration to a patient. Suitably, the solid compositions described herein are prepared as single uniform solid dispersion and are swallowed whole.

A further aspect of the invention is a method for preparing a modified release benzonatate composition. The method involves (a) adsorbing benzonatate onto a porous silicon dioxide to form a benzonatate adsorbate powder; (b) admixing a benzonatate adsorbate powder with a water-soluble polyethylene oxide resin in an amount effective to provide a modified release profile to the benzonatate and optional excipients to form a homogenous solid dispersion; (c) compressing the homogenous solid dispersion into a tablet core; and (d) coating the tablet core with at least one bucco-protective coating. In one embodiment, the adsorbate powder components are passed through a 425 micron screen prior to compression. Optionally, other excipients may be passed through a similar size or other screens prior to admixture. For example, polyethylene oxide particles may be passed through a larger screen size (e.g., 600 micron), whereas a lubricant (e.g., magnesium stearate) may be passed through a smaller screen (e.g., about 250 microns). Optionally, the tablet is coated with a pH-dependent coating prior to coating with the bucco-protective coating. This pH-dependent coated-tablet core may be cured following coating with the reverse enteric coating. Suitable curing conditions are known and may include, e.g., heating at 40° C. to 50° C. for 30 minutes to two hours. In one embodiment, the total tablet core is about 600 mg to about 900 mg. In another embodiment, mini-tablets are prepared which are in loaded into a capsule to provide an approximately equivalent amount of benzonatate.

As previously described herein, a modified release benzonatate provides therapeutically effective benzonatate plasma levels over a period in excess of the immediate release benzonatate profile; which immediate release provides benzonatate for about 6 to 8 hours. Thus, a modified release composition provides an effective amount of benzonatate for at least about 10 hours to about 12 hours, up to about 24 hours. As used herein in connection with other pharmaceutically active drugs which may be combined with the benzonatate, the term "modified release" refers to compositions which provide effective amounts at least one of the active components (other than benzonatate) over a period of at least about 8 hours, and preferably up to about 24 hours. For a 24 hour release product, in one aspect, less than 50% of an active component is released at about 12 hours from administration. In another aspect, less than 60% of an active component is released at about 12 hours from administration. In still another aspect, less than 70% of an active component is released at about 12 hours. In still other embodiments, less than about 80% or more of an active component is released at about 12 hours. The term "modified release" may include, e.g., compositions which are extended release formulations, sustained release formulations, or delayed release formulations. The release profile may be assessed using in vitro dissolution assays known to those of skill in the art [e.g., USP basket method or Paddle Method, or channel flow method]. The release profile may be assessed in vivo (e.g., for bioavailability determinations), using plasma concentrations to assess maximum concentration ($C_{max}$) and area under the curve (AUC). Such assays are well known to those of skill in the art.

In another embodiment, a benzonatate tablet or powder composition as defined herein is characterized by having an in vitro profile as follows: At 0.33 hour, % release is 0 to about 1% release, or an arithmetic average of about 0.25% release; at 1 hour, percent release is about 4 to about 16% release, or about 10.75% release; at 2 hours, percent release is about 20% to about 33% release, or about 27.62% release; at 6 hours, percent release is about 60% to about 89%, or about 79%; at 8 hours, percent benzonatate release is about 73% to about 102%, or about 95.62%, and at 12 hours, benzonatate release is about 90% to about 103% release, or about 100% release, as determined in an in vitro assay in 0.1 N HCl dissolution medium as described herein.

In certain embodiments, a modified release benzonatate composition provides an in vitro release, wherein there is no more than about 50% release of the benzonatate within 1 hour, no more than about 50% to about 80% release within 6 hours, and no less than about 80% release at 12 hours, as determined in an in vitro dissolution assay and substantially no benzonatate release from the composition in the buccal cavity or esophagus. In another example, a benzonatate composition as described herein provides an in vitro release, wherein there is substantially no benzonatate release from the composition in the buccal cavity or esophagus.

In one embodiment, this in vitro dissolution profile is that of the reverse enteric coated tablet comprising a benzonatate adsorbate. This may be assessed using the Paddle apparatus at 50 rpm, in a dissolution medium of 500 mL 0.1 N HCl for about 1 hour, which is then adjusted to a pH of about 6.8 with a phosphate buffer, at a temperature of 37° C. An alternative assay involves using the following dissolution parameters: Paddle apparatus, 50 rpm, Medium: 0.05 M sodium phosphate, pH 6.8 (900 mL), temperature 37° C., or another suitable assay.

In one embodiment, a 12-hour benzonatate composition as provided herein is characterized by having an in vitro dissolution, at 0.335 hour, % release is 0 to about 1% release, or an arithmetic average of about 0.25% release; at 1 hour, percent release is about 4 to about 16% release, or about 11% release; at 2 hours, percent release is about 20% to about 33% release, or about 28% release; at 6 hours, percent release is about 60% to about 89%, or about 79%; at 8 hours, percent benzonatate release is about 73% to about 102%, or about 96%, and at 12 hours, benzonatate release is about 90% to about 103% release, or about 100% release, as determined in an in vitro assay in 0.1 N HCl dissolution medium as described herein In another embodiment, rather than being compressed into a tablet, the benzonatate modified release powder can be loaded into a hard shell capsule. Suitable hard shell capsules include standard two piece gelatin capsules which typically range from about 10 to about 88 mm when fitted together (locked length). While capsules may have increased risk of disuse, such capsules facilitate the combination of an additional pharmaceutically active ingredient which is in immediate release form or in a modified form but which is not within the solid dispersion of the waxy matrix. One of skill in the art can readily prepare these capsules given the guidance provided herein, in view of that which is known to those of skill in the art.

Method of Treating Cough and Cold Symptoms

In one aspect, the compositions described herein are useful for symptomatic relief of coughs for at least 8 hours to about 12 hours, or 10 hours to 12 hours, following administration of a single oral dose of a benzonatate modified release solid oral tablet or capsule composition as described herein. The compositions provide convenience for patients with cough symptoms, as presently available immediate release compositions are 8 hour products. Further, since the compositions provide the modified release benzonatate in tablet or capsule form, these compositions reduce the risk of major oropharyngeal anesthesia side effects resulting from accidental chewing or crushing associated with the softgel forms of benzonatate.

A method of delivering a daily dose of a benzonatate composition(s) described herein to a patient in need thereof is provided. Typically, benzonatate is used to treat coughs caused by the common cold and other breathing problems (e.g., pneumonia, bronchitis, emphysema, asthma).

In children and adults, a daily dose may be about 100 mg to about 300 mg per dose, with a daily dose of about 200 mg to about 600 mg per day (daily dose).

In one embodiment, the patient receives a daily dose of a benzonatate composition(s) containing about 75 mg to about 600 mg benzonatate in a solid oral composition as provided herein, or values therebetween. In certain embodiments, the daily dose may be in the range of about 100 mg per day to about 400 mg per day, or about 150 mg per day to about 300 mg per day.

A benzonatate tablet or capsule (e.g., benzonatate mini-tablet(s) in a capsule) as described herein may be dosed with one or two tablets, or one or two capsules for each dose. In other words, a single dose may be 1-2 tablets or capsules. In certain embodiments, a patient is dosed once or twice per day at about 12 hour intervals (no more than two times/day).

In certain embodiments, a single dose for children (under 12 or under 18) is a single tablet or capsule. In other embodiments, a single dose for adults is a single tablet or capsule (12 and over or 18 and over). In still other embodiments, a single dose for adults is two tablets or capsules.

The following examples are provided to more specifically illustrate the compositions of the present invention and not intended to be limiting. They are for illustrative purposes only and it is realized that changes and variations can be made without departing from the spirit and scope of the invention.

EXAMPLES

Example 1: Bucco-Protective, Reverse-Enteric Coated Benzonatate—Silicon Dioxide Adsorbate with Polyethylene Oxide Modified Release Matrix Tablet

TABLE 1

| Sr. # | Ingredient | mg/tab |
|---|---|---|
| | Core Tablets | |
| 1. | Benzonatate | 150.00 |
| 2. | Silicon Dioxide (Syloid ® XDP 3150) | 100.00 |
| 3. | Isomalt (Galen IQ 720) | 348.00 |
| 4. | Polyethylene Oxide (Polyox ® WSR 1105 NEO) | 250.00 |
| 5. | Magnesium stearate NF | 2.00 |
| | Coating 1 (Bucco-Protective (Reverse Enteric)) | |
| 6. | Amino Methacrylate copolymer (Eudragit ® E PO ReadyMix) | 68.00 |
| 7. | Purified Water * | — |
| | Coating 2 (Non-functional) | |
| 8. | Opadry ® II White | 27.54 |
| 9. | Purified Water * | — |

* Purified water is not present in final product. Evaporates during processing.

A. Tablet Core

Benzonatate was added gradually to silicon dioxide in a high shear mixer and mixed to distribute uniformly. The powder blend was passed through 425 micron screen and loaded into a blender. Isomalt (passed through 425 micron screen) and polyethylene oxide (passed through 710 micron screen) were added into the blender and mixed for 5 minutes. Magnesium stearate (passed through 250 micron screen) was added and mixed for 5 minutes. Tablets were compressed on a rotary tablet press using appropriate tooling to target tablet weight of 850 mg Tablet hardness: 10-11 kp.

B. Coating 1

Eudragit® E PO [Eudragit® E PO ReadyMix (Evonik) contains butylated methacrylate copolymer, sodium lauryl sulfate, stearic acid, talc, silicon dioxide] was added to purified water and mixed using a propeller mixer for 30 minutes. The coating dispersion was passed through 425 micron screen. Coating was performed on the core tablets in perforated coating pan until 8% w/w solid weight gain level. The process parameters were as follows: Inlet temperature: 29° C.-33° C., Exhaust temperature: 25° C.-28° C., air flow: 61 cfm, spray rate: 3.2 g/minutes. Tablets were allowed to cure in hot air oven at 40° C. for 2 hours.

C. Coating 2

The coating dispersion was prepared by adding Opadry II White powder [Opadry II White (Colorcon) contains polyvinyl alcohol, polyethylene glycol, talc] to purified water under stirring and further allowed to stir for 45 minutes. Coating was performed on the Eudragit® E PO coated tablets in a perforated coating pan. The coating process parameters were as follows: inlet temperature: 51° C.-53° C., exhaust temperature: 42° C.-43° C., air flow: 73 cfm, spray rate: 2.0 g/minutes.

Example 2: Bucco-Protective, Reverse-Enteric Coated Benzonatate—Silicon Dioxide Adsorbate with Hydrophilic Modified Release Matrix Tablet—Formulation 2

TABLE 2

| Sr. # | Ingredient | mg/tab |
|---|---|---|
| | Core Tablets | |
| 1. | Benzonatate | 150.00 |
| 2. | Silicon Dioxide (Syloid ® XDP 3150) | 100.00 |
| 3. | Microcrystalline cellulose (Avicel ® PH 102) | 338.00 |
| 4. | Copovidone (Kollidon ® VA 64 Fine) | 30.00 |
| 5. | Hypromellose (Methocel ™ K100 LV Premium CR) | 230.00 |
| 6. | Magnesium stearate | 2.00 |
| | Coating 1 (Bucco-protective, Reverse Enteric) | |
| 6. | Amino Methacrylate copolymer (Eudragit ® E PO ReadyMix Clear) | 68.00 |
| 7. | Purified Water * | |
| | Coating 2 (Non-functional) | |
| 8. | Opadry ® II White | 27.4 |
| 9. | Purified Water * | — |

* Purified water is not present in final product. Evaporates during processing.

A. Tablet Cores

Benzonatate was added gradually to Silicon Dioxide in high shear mixer and mixed to distribute uniformly. The powder blend was passed through mesh 425 micron screen and loaded into a blender. Microcrystalline cellulose, Kollidon VA64 and Hypromellose (passed through 425 micron screen) were added into the blender and mixed for 5 minutes. Magnesium stearate (passed through 250 micron screen) was added and lubricated for 5 minutes. Tablets were compressed on a rotary tablet press using appropriate tooling to target tablet weight of 850 mg.

B. Coating 1

Eudragit® E PO is added to Purified water and mixed using a propeller mixer for 30 minutes. The coating dispersion was passed through a 425 micron screen. Coating was performed on the core tablets in perforated coating pan till 8% w/w solid weight gain level. The process parameters were as follows: Inlet Temperature: 29° C.-33° C., Exhaust Temp: 25° C.-28° C., Air flow: 61 cfm, Spray rate: 3.2 g/minutes. Tablets were cured in hot air oven at 40° C. for 2 hours.

C. Coating 2

The coating dispersion was prepared by adding Opadry II White powder to Purified water under stirring and further allowed to stir for 45 minutes. Coating was performed on the Eudragi®t E PO coated tablets in a perforated coating pan. The coating process parameters were as follows: Inlet Temperature: 51° C.-53° C., Exhaust Temp: 42° C.-43° C., Air flow: 73 cfm, Spray rate: 2.0 g/minutes.

Example 3: Bucco-Protective Coated Benzonatate—Silicon Dioxide Adsorbate with Polyethylene Oxide Modified Release Matrix Tablet

TABLE 3

| Sr. # | Ingredient | mg/tab |
|---|---|---|
| | Core Tablets | |
| 1. | Benzonatate | 150.00 |
| 2. | Silicon Dioxide (Syloid ® XDP 3150) | 100.00 |
| 3. | Isomalt (Galen ® IQ 720) | 348.00 |
| 4. | Polyethylene Oxide (Polyox ® WSR 1105 NEO) | 250.00 |
| 5. | Magnesium stearate | 2.00 |
| | Bucco-Protective Coating | |
| 6. | Zein | 13.8 |
| 7. | Povidone ® K-30 | 5.9 |
| 8. | Propylene glycol | 1.4 |
| 9. | Talc | 4.1 |
| 10. | Ethanol (70% v/v)* | 118.9 |

*Ethanol is not present in final product. Evaporates during processing.

The tablet cores were prepared according to the process of Example 1 and compressed to a tablet hardness: 10-11 kp.

For coating, the povidone was dissolved in part of ethanol. Zein was then added and stirred until dissolved. Propylene glycol was added to remaining ethanol and mixed. Talc was then added and homogenized. Both the liquids were mixed and utilized for coating.

Tablets were coated using the above dispersion in a perforated coating pan. The coating process parameters were as follows: Inlet Temperature: 35° C.-40° C., Exhaust Temp: 29° C.-32° C., Air flow: 56 cfm, Spray rate: 0.8 g/minutes.

Example 4: Bucco-Protective Coated Benzonatate—Silicon Dioxide Adsorbate with Polyethylene Oxide Modified Release Matrix Tablet

TABLE 4

| Sr. # | Ingredient | mg/tab |
|---|---|---|
| | Core Tablets | |
| 1. | Benzonatate | 150.00 |
| 2. | Silicon Dioxide (Syloid ® XDP 3150) | 100.00 |
| 3. | Isomalt (Galen ® IQ 720) | 348.00 |
| 4. | Polyethylene Oxide (Polyox ® WSR 1105 NEO) | 250.00 |
| 5. | Magnesium stearate | 2.00 |
| | Bucco-Protective Coating | |
| 6. | Aquarius ® MG | 150.00 |
| 7. | Purified water | 850.00 |

* Purified water is not present in final product. Evaporates during processing.

The tablet core was prepared using the process described in Example 1 and compresses to a tablet hardness: 10-11 kp. Aquarius® MG [mixture of cellulose and wax] was mixed with purified water using overhead stirrer and stirred for 60 minutes. Tablets were coated using the above coating dispersion in a perforated coating pan. The coating process parameters were as follows: Inlet Temperature: 63° C.-65° C., Exhaust Temp: 44° C.-48° C., Air flow: 65 cfm, Spray rate: 2.5 g/minutes.

Example 5: Bucco-Protective Coated Benzonatate—Silicon Dioxide Adsorbate with Polyethylene Oxide Modified Release Matrix Tablet

TABLE 5

| Sr. # | Ingredient | mg/tab |
|---|---|---|
| | Core Tablets | |
| 1. | Benzonatate | 150.00 |
| 2. | Silicon Dioxide (Syloid ® XDP 3150) | 100.00 |
| 3. | Isomalt (Galen ® IQ 720) | 348.00 |
| 4. | Polyethylene Oxide (Polyox WSR 1105 NEO) | 250.00 |
| 5. | Magnesium stearate | 2.00 |
| | Bucco-Protective Coating | |
| 6. | Aquapolish ® D | 90.00 |
| 7. | Purified water | 510.00 |

* Purified water is not present in final product. Evaporates during processing.

The tablet cores were prepared using the above ingredients and the method of Example 1, to a tablet hardness: 10-11 kp. Aquapolish® D [Hypromellose, hydroxypropyl cellulose, stearic acid, talc and vegetable oil] was added gradually to purified water and mixed for 60 minutes. Tablets were coated using the above coating dispersion in a perforated coating pan. The coating process parameters were as follows: Inlet Temperature: 49° C.-52° C., Exhaust Temp: 39° C.-41° C., Air flow: 63 cfm, Spray rate: 1.6 g/minutes.

Example 6: Bucco-Protective Coated Benzonatate—Silicon Dioxide Adsorbate with Polyethylene Oxide Modified Release Matrix Tablet

TABLE 6

| Sr. # | Ingredient | mg/tab |
|---|---|---|
| | Core Tablets | |
| 1. | Benzonatate | 150.00 |
| 2. | Silicon Dioxide (Syloid ® XDP 3150) | 100.00 |
| 3. | Isomalt (Galen ® IQ 720) | 348.00 |
| 4. | Polyethylene Oxide (Polyox ™ WSR 1105 NEO) | 250.00 |
| 5. | Magnesium stearate | 2.00 |
| | Bucco-Protective Coating | |
| 6. | Opadry ® TM | 60.00 |
| 7. | Purified water | 540.00 |

* Purified water is not present in final product. Evaporates during processing.

The tablet cores were prepared using components 1-5 above and the process described in Example 1, with compression to a tablet hardness: 10-11 kp.

The bucco-protective coating was Opadry® TM [mixture of HPMC 2910 (viscosity grades 3 mPas to 50 mPas), talc, titanium dioxide, macrogol, saccharin sodium, colorant], which was added gradually to purified water while stirring and mixed for 45 minutes. Tablets were coated using the above coating dispersion in a perforated coating pan. The coating process parameters were as follows: Inlet Temperature: 64° C.-67° C., Exhaust Temp: 47° C.-49° C., Air flow: 64 cfm, Spray rate: 2.5 g/minutes.

Example 7: Bucco-Protective Coated Benzonatate—Silicon Dioxide Adsorbate with Polyethylene Oxide Modified Release Matrix Tablet

TABLE 7

| Sr. # | Ingredient | mg/tab |
|---|---|---|
| | Core Tablets | |
| 1. | Benzonatate | 150.00 |
| 2. | Silicon Dioxide (Syloid ® XDP 3150) | 100.00 |
| 3. | Isomalt (GalenIQ ® 720) | 348.00 |
| 4. | Polyethylene Oxide (Polyox ® WSR 1105 NEO) | 250.00 |
| 5. | Magnesium stearate | 2.00 |
| | Bucco-Protective Coating | |
| 6. | Certiseal ® FC300 | 140.00 |
| 7. | Talc | 12.00 |
| 8. | Purified water | 140.00 |

* Purified water is not present in final product. Evaporates during processing.

The tablet core was prepared using components 1-5 above and the process described in Example 1, with compression to a tablet hardness: 10-11 kp.

The bucco-protective coating was Certiseal® FC300 [shellac based aqueous coating system, Mantrose-Haeuser]. Certiseal® was added to purified water while stirring and further mixed for 30 minutes. Talc was added to the above and homogenized for 10 minutes. Tablets were coated using the above coating dispersion in a perforated coating pan. The coating process parameters were as follows: Inlet Temperature: 63° C.-64° C., Exhaust Temp: 45° C.-49° C., Air flow: 64 cfm, Spray rate: 1.6 g/minutes.

Example 8: Bucco-Protective Coated Benzonatate—Silicon Dioxide Adsorbate with Polyethylene Oxide Modified Release Matrix Tablet

TABLE 8

| Sr. # | Ingredient | mg/tab |
|---|---|---|
| | Core Tablets | |
| 1. | Benzonatate | 150.00 |
| 2. | Silicon Dioxide (Syloid ® XDP 3150) | 100.00 |
| 3. | Isomalt (Galen ® IQ 720) | 348.00 |
| 4. | Polyethylene Oxide (Polyox ™ WSR 1105 NEO) | 250.00 |
| 5. | Magnesium stearate | 2.00 |
| | Bucco-Protective Coating | |
| 6. | ReadiLycoat ® | 90.00 |
| 7. | Purified water | 510.00 |

* Purified water is not present in final product. Evaporates during processing.

The tablet core was prepared using components 1-5 above and the process described in Example 1, with compression to a tablet hardness: 10-11 kp.

The bucco-protective coating was ReadiLYCOAT® [modified pea starch based coating system, Roquette]. ReadiLYCOAT® was gradually added to purified water and stirred for 30 minutes. Tablets were coated using the above coating dispersion in a perforated coating pan. The coating process parameters were as follows: Inlet Temperature: 50° C.-53° C., Exhaust Temp: 35° C.-37° C., Air flow: 57 cfm, Spray rate: 1.4 g/minutes.

Example 9: EVALUATION OF COATED TABLETS

The drug release from coated tablets prepared according to Examples 1 to 8 was assessed using a biorelevant dissolution medium. This in-vitro dissolution was conducted in USP paddle apparatus, 50 rpm using simulated saliva, 900 mL at 37° C. for 20 minutes followed by change in medium to 900 mL 0.1N hydrochloric acid at 37° C. up to 12 hours. The time period of 20 minutes was selected as the extreme case scenario for the dosage form to be exposed to saliva in the buccal cavity. The tablets with different coating materials demonstrated no drug release in 10 minutes and less than 1% or no release in 20 minutes indicating that there will not be premature release of the drug in the oral cavity. As a reference, the uncoated tablet was also tested in simulated saliva and it releases about 3% in 20 minutes. Table 9 below shows that the formulation tested lots of the formulation of Examples 1 to 8 are listed) exhibited extended release of benzonatate up to about 8 to 12 hours in 0.1N HCl dissolution medium.

TABLE 9

Dissolution screening results in simulated saliva fluid (20 minutes) followed by change to 0.1N HCl, 37° C., USP Paddle, 50 rpm.

| | % Benzonatate release | | | | | |
|---|---|---|---|---|---|---|
| Time (h) | 0.33 h | 1 h | 2 h | 6 h | 8 h | 12 h |
| Example 1 | 0 | 13 | 27 | 79 | 97 | 100 |
| Example 2 | 0 | 16 | 26 | 60 | 73 | 90 |
| Example 3 | 0 | 8 | 24 | 71 | 93 | 102 |
| Example 4 | 0 | 4 | 20 | 72 | 98 | 102 |
| Example 5 | 0 | 9 | 29 | 86 | 102 | 103 |
| Example 6 | 0 | 10 | 30 | 86 | 101 | 103 |
| Example 7 | 1 | 13 | 32 | 89 | 100 | 100 |
| Example 8 | 0 | 12 | 27 | 86 | 100 | 102 |

Stability studies were conducted at accelerated (40° C./75% RH) and long-term (25° C./60% RH) storage conditions using Example 1. The results of the in-vitro dissolution of initial and on stability are given in Table 10 below. There is reproducible dissolution at accelerated and long-term conditions and with no alteration in in-vitro dissolution profiles on storage.

TABLE 10

In-vitro Dissolution Profiles (Stability Studies)

| Stability Condition (° C./% relative humidity (RH))/Timepoint | % Benzonatate release | | | | | | | |
|---|---|---|---|---|---|---|---|---|
| Time | 0.5 h | 1 h | 2 h | 3 h | 4 h | 6 h | 8 h | 10 h |
| Initial | 6 | 13 | 27 | 41 | 55 | 79 | 97 | 100 |
| 40° C./75% 1 M | 6 | 13 | 26 | 40 | 51 | 74 | 93 | 95 |
| 40° C./75% 2 M | 7 | 14 | 28 | 41 | 55 | 80 | 100 | 102 |
| 40° C./75% 3 M | 6 | 13 | 26 | 39 | 52 | 76 | 95 | 97 |
| 40° C./75% 6 M | 8 | 16 | 32 | 47 | 61 | 84 | 98 | 100 |
| 25° C./60% 1 M | 7 | 14 | 28 | 42 | 54 | 76 | 92 | 94 |
| 25° C./60% 2 M | 6 | 13 | 27 | 41 | 54 | 78 | 96 | 98 |
| 25° C./60% 3 M | 6 | 13 | 28 | 42 | 56 | 81 | 100 | 102 |
| 25° C./60% 6 M | 7 | 15 | 30 | 44 | 58 | 82 | 97 | 99 |

(M - Month, h - hour)

Example 10: Demonstration of Alcohol Resistance of Benzonatate Extended Release Tablets Administration of controlled release dosage forms with alcoholic beverages is a major concern since ethanol is known to dissolve certain rate-controlling components. In many cases, it leads to dose-dumping. The ethanol test was performed on benzonatate extended release tablets 150 mg. The alcohol effect was evaluated for the developed product by conducting in-vitro dissolution studies in 40% ethanol in 0.1 N hydrochloric acid 37° C., USP Paddle apparatus, 50 rpm.

TABLE 11

Test for effect of Alcohol (Dose-dumping Study).

| | % Benzonatate release | | |
|---|---|---|---|
| Time (h) | 0.5 h | 1 h | 2 h |
| 0.1N HCl | 6 | 13 | 26 |
| 40% Ethanol in 0.1N HCl | 1 | 5 | 13 |

It can be seen from this study that in presence of alcohol, only half the quantity of benzonatate is released as compared to the release in dissolution medium without alcohol. No dose-dumping occurred. Thus, the presence of alcohol slowed the release of drug from the test formulation.

Example 11—Pharmacokinetic Pilot Study

An open-label, randomized, three-period cross-over, single-day pilot study to evaluate the pharmacokinetics of Benzonatate extended-release tablets under fed and fasted conditions and to compare with an equivalent dose of an immediate release product (Tessalon®) under fed conditions. The study was conducted in healthy adult subjects. The Test product treatment was Benzonatate Extended Release Tablets 150 mg (prepared as in Example 1). The dosing regimen was 2 tablets of 150 mg dosed at 0 hr and 12 hr (total dose: 600 mg). The product was administered under fasting and fed conditions. The Reference treatment was Tessalon® (Benzonatate Immediate Release Perles) 100 mg dosing of 2 perles of 100 mg dosed at 0 hr, 8 hr, and 16 hr (total dose: 600 mg) under fed conditions. Blood samples were collected at predetermined time periods. The plasma samples were analysed for benzonatate using a validated bioanalytical method. The relative mean plasma benzonatate $AUC_t$, $AUC_{inf}$ and $C_{max}$, were calculated using statistical software program. Results of the pharmacokinetic study are given in the Table 12 below.

In this study, pharmacokinetics were evaluated over a 24-hour period in which the test drug using the following parameters.

$C_{max}$: Maximum measured analyte concentration over the sampling period.

$T_{max}$: Time of the maximum measured analyte concentration over the sampling period.

$AUC_{inf}$: The area under the analyte concentration versus time curve from time zero to infinity. $AUC_{inf} = AUC_t + Ct/Kel$, where Ct is the last measurable analyte concentration.

TABLE 12

Results of Pharmacokinetic Data (Pilot Study)

| Pharmacokinetic Parameter | Test (Fasting) | Test (Fed) | Reference (Fed) |
|---|---|---|---|
| Cmax (ng/ml) | 32.7 | 43.7 | 65.6 |
| | 33.2 | 35.3 | 61.1 |
| AUC0-t (ng * h/ml) | 271 | 222 | 177 |
| | 284 | 193 | 187 |

TABLE 12-continued

Results of Pharmacokinetic Data (Pilot Study)

| Pharmacokinetic Parameter | Test (Fasting) | Test (Fed) | Reference (Fed) |
|---|---|---|---|
| $AUC_{0-inf}$ (ng * h/ml) | 272 | 202 | 173 |
|  | 247 | 186 | 161 |
| Tmax (h) | 4.00 | 8.00 | 0.70 |
|  | (1.50-16.33) | (3.00-19.00) | (0.33-16.67) |

Note:
For Cmax and AUC, Arithmetic mean (top) and Geometric mean (below).

Example 12: Benzonatate Extended-Release Tablets, 150 mg

| Sr. # | Ingredient | Mg/tab |
|---|---|---|
|  | Core Tablet |  |
| 1 | Benzonatate, USP | 150.00 |
| 2 | Silicon Dioxide NF (Syloid ® XDP 3150) | 100.00 |
| 3 | Isomalt NF (Galen IQ 720) | 428.00 |
| 4 | Polyethylene Oxide NF (Polyox ® WSR 1105 NEO) | 170.00 |
| 5 | Magnesium Stearate NF | 2.00 |
|  | Coating 1 (Bucco-Protective (Reverse Enteric)) |  |
| 6 | Amino Methacrylate copolymer (Eudragit ® E PO ReadyMix) | 68.00 |
| 7 | Purified Water* | — |

*Purified water is not present in final product (evaporates during the processing).

A. Tablet core: Benzonatate is added gradually to Silicon Dioxide in a high shear mixer and mixed to distribute uniformly. The powder blend is passed through a 600 micron screen and loaded into a blender. Isomalt and Polyethylene oxide are passed through a 600 micron screen and added to the blender and mixed for 20 minutes. Magnesium stearate (passed through a 250 micron screen) is added and lubricated for 7 minutes. Tablets are compressed on a rotary tablet press using appropriate tooling to a target tablet weight of 850 mg. Tablet hardness: 10-13 kp B. Coating 1: Eudragit® E PO [Eudragit® E PO Ready-Mix (Evonik) contains butylated methacrylate copolymer, Sodium lauryl sulfate, Stearic acid, Talc, Silicon dioxide] is added to Purified water and mixed using a propeller mixer for 60 minutes. The coating dispersion is sifted through a 425 micron screen. Coating is performed on the core tablets in a perforated coating pan until 8% solid weight gain level. The process parameters are as follows: Inlet temperature: 30° C.-40° C., Exhaust Temp.: 25° C.-35° C., Air flow: 55-65 cfm, Spray rate: 1.0-3.0 g/minutes. Tablets are allowed to cure in a hot air oven at 40° C. for 2 hours.

Example 13: Benzonatate Extended-Release Tablets, 150 mg

| Sr. # | Ingredient | Mg/tab |
|---|---|---|
|  | Core Tablet |  |
| 1 | Benzonatate, USP | 150.00 |
| 2 | Silicon Dioxide NF (Syloid ® XDP 3150) | 100.00 |
| 3 | Isomalt NF (Galen IQ 720) | 428.00 |
| 4 | Polyethylene Oxide NF (Sentry ® Polyox WSR 1105 NEO) | 170.00 |
| 5 | Magnesium Stearate NF | 2.00 |
|  | Coating 1 (Bucco-Protective) |  |
| 6 | Ethylcellulose Aq. dispersion, Type B (Surelease ® E-7 19040 Clear)* | 41.61** |
| 7 | Hypromellose (Methocel E 5 LV) | 0.89 |
| 8 | Purified Water*** |  |

*Contains 25% w/w solids
**Represents the solid content
***Purified water is not present in final product (evaporates during the processing)

A. Tablet core: Benzonatate is added gradually to Silicon Dioxide in a high shear mixer and mixed to distribute uniformly. The powder blend is passed through a 600 micron screen and loaded into a blender. Isomalt and Polyethylene oxide are passed through a 600 micron screen and added to the blender and mixed for 20 minutes. Magnesium stearate (passed through a 250 micron screen) is added and lubricated for 7 minutes. Tablets are compressed on a rotary tablet press using appropriate tooling to target a tablet weight of 510 mg. Tablet hardness: 10-13 kp.

B. Coating 1: Hypromellose [Methocel® E 5 LV (Colorcon)] is weighed and dissolved in the weighed quantity of purified water using an overhead stirrer. Ethylcellulose aqueous dispersion [Surelease® E-7 19040 Clear (Colorcon) contains Ethylcellulose, Medium chain triglycerides, Oleic acid, Ammonium hydroxide and Purified water] is weighed and the Hypromellose solution is added to it gradually under stirring. The stirring was continued for 60 minutes. The coating dispersion is sifted through a 425 micron screen. Coating was performed on the core tablets in a perforated coating pan until 5% solid weight gain level. The process parameters are as follows: Inlet temperature: 50° C.-63° ~C, Exhaust Temp.: 40° C.-45° C., Air flow: 55-65 cfm, Spray rate: 0.5-2.0 g/minutes. Tablets are allowed to cure in a hot air oven at 60° C. for 6 hours.

Dissolution results in simulated saliva fluid (30 minutes)

| Time (h) |  | 0.5 |
|---|---|---|
| % Drug release | Example 1 | 0 |
|  | Example 2 | 0 |

Example 14: Benzonatate Extended-Release Tablets, 150 mg

| Sr. # | Ingredient | Mg/tab |
|---|---|---|
|  | Core Tablet |  |
| 1 | Benzonatate, USP | 150.00 |
| 2 | Silicon Dioxide NF (Syloid ® 244 FP) | 150.00 |
| 3 | Isomalt NF (Galen ® IQ 721) | 250.00 |
| 4 | Microcrystalline Cellulose NF (Avicel ® PH 102) | 148.50 |
| 5 | Polyethylene Oxide NF (Sentry ® Polyox WSR Coagulant) | 100.00 |
| 6 | Magnesium Stearate NF | 1.50 |

-continued

| Sr. # | Ingredient | Mg/tab |
|---|---|---|
| | Coating 1 (Bucco-Protective) | |
| 6 | Polyvinyl Acetate Dispersion 30% (Kollicoat ® SR 30D)* | 31.35** |
| 7 | Povidone USP (Kollidon ® 30) | 0.65 |
| 8 | Purified Water*** | — |
| | Coating 2 (non-functional) | |
| 8 | Opadry ™ II Clear | 16.00 |
| 9 | Purified Water*** | — |

*Contains 25% w/w solids
**Represents the solid content
***Purified water is not present in final product (evaporates during the processing)

A. Tablet core: Add Benzonatate gradually to Silicon Dioxide in a high shear mixer and mix to distribute uniformly. Sift the powder blend through a 600 micron screen and load into a blender. Weigh Isomalt, Microcrystalline cellulose and Polyethylene oxide and sift through a 600 micron screen. Add to the blender and mix for 10 minutes. Weigh Magnesium stearate and sift through a 250 micron screen. Add to the blend and mix for 5 minutes. Compress the tablets on a rotary tablet press using appropriate tooling to target tablet weight of 800 mg at a tablet hardness of about 8-10 kp.

B. Coating 1: Weigh Povidone [Kollidon® 30 (BASF)] and dissolve in the weighed quantity of purified water using an overhead stirrer. Weigh Polyvinyl acetate dispersion 30% [Kollicoat® SR 30D (BASF) contains Polyvinyl acetate, Povidone Sodium lauryl sulphate and Purified water] and with stirring using overhead stirrer add the Povidone solution to it gradually. Continue stirring for 60 minutes. Sift the coating dispersion through a 425 micron screen and coat the core tablets in a performed coating pan until 4% solid weight gain level using coating process parameters specified as: Inlet temperature: 35° C.-45° C., Exhaust Temp.: 29° C.-34° C., Air flow: 55-65 cfm, Spray rate: 0.5-2.0 g/minutes.

Cure the coated tablets in hot air oven at 60° C. for 5 hours.

C. Coating 2: Prepare the coating dispersion by dispersing the Opadry® II Clear powder [Opadry® II Clear (Colorcon) contains Polyvinyl alcohol, Polyethylene glycol, Talc] in Purified water under stirring. Continue stirring for 45 minutes. Sift the coating dispersion through a 425 micron screen and carry out the coating of the Polyvinyl acetate coated tablets in a perforated coating pan for 3% solid weight gain level using the coating process parameters specified as: Inlet temperature: 60° C.-70° C., Exhaust Temp.: 42° C.-45° C., Air flow: 60-70 cfm, Spray rate: 0.5-2.0 g/minutes.

Example 15: Benzonatate Extended-Release Tablets, 90 mg

| Sr. # | Ingredient | Mg/tab |
|---|---|---|
| | Core Tablet | |
| 1 | Benzonatate, USP | 90.00 |
| 2 | Silicon Dioxide NF (Syloid ® XDP 3050) | 70.00 |
| 3 | Isomalt NF (Galen ® IQ 721) | 185.00 |
| 4 | Polyethylene Oxide NF (Polyox ® WSR 205 NEO) | 163.50 |
| 5 | Magnesium Stearate NF | 1.50 |

-continued

| Sr. # | Ingredient | Mg/tab |
|---|---|---|
| | Coating 1 (Bucco-Protective (Reverse Enteric)) | |
| 6 | Amino Methacrylate copolymer (Eudragit ® E PO ReadyMix) | 40.80 |
| 7 | Purified Water* | — |
| | Coating 2 (non-functional) | |
| 8 | Opadry II Clear | 16.50 |
| 9 | Purified Water* | — |

*Purified water is not present in final product (evaporates during the processing).

A. Tablet core: Add Benzonatate gradually to Silicon Dioxide in a high shear mixer and mix to distribute uniformly. Sift the powder blend through a 600 micron screen and load into a blender. Weigh Isomalt, Microcrystalline cellulose and Polyethylene oxide and sift through a 600 micron screen. Add to the blender and mix for 10 minutes. Weigh Magnesium stearate and sift through a 250 micron screen. Add to the blend and mix for 5 minutes. Compress the tablets on a rotary tablet press using appropriate tooling to a target tablet weight of 510 mg at a tablet hardness of about 5-8 kp.

B. Coating 1: Add Eudragit E PO [Eudragit® E PO ReadyMix (Evonik) contains Butylated methacrylate copolymer, Sodium lauryl sulfate, Stearic acid, Talc, Silicon dioxide] to Purified water gradually under stirring using a propeller mixer and continue stirring for 60 minutes. Sift the coating dispersion through a 425 micron screen. Coat the core tablets with the coating dispersion in a perforated coating pan until 8% solid weight gain level using the specified process parameters as: Inlet temperature: 32° C.-40° C., Exhaust Temp.: 29° C.-34° C., Air flow: 58-64 cfm, Spray rate: 0.5-2.0 g/minutes.

Cure the coated tablets in a hot air oven at 40° C. for 2 hours.

C. Coating 2: Prepare the coating dispersion by dispersing the Opadry® II Clear powder [Opadry® II Clear (Colorcon) contains Polyvinyl alcohol, Polyethylene glycol, Talc] in Purified water under stirring. Continue stirring for 45 minutes. Sift the coating dispersion through a 425 micron screen and carry out the coating of the Polyvinyl acetate coated tablets in a perforated coating pan for 3% solid weight gain level using the coating process parameters specified as: Inlet temperature: 62° C.-68° C., Exhaust Temp.: 42° C.-45° C., Air flow: 63-68 cfm, Spray rate: 0.5-1.5 g/minutes.

Example 16: Benzonatate Extended-Release Tablets, 75 mg

| Sr. # | Ingredient | mg/tab |
|---|---|---|
| | Core Tablet | |
| 1 | Benzonatate, USP | 75.00 |
| 2 | Silicon Dioxide NF (Syloid ® XDP 3150) | 50.00 |
| 3 | Isomalt NF (Galen IQ 720) | 214.00 |
| 4 | Polyethylene Oxide NF (Polyox ® WSR 1105 NEO) | 85.00 |
| 5 | Magnesium Stearate NF | 1.00 |
| | Coating 1 (Bucco-Protective (Reverse Enteric)) | |
| 6 | Amino Methacrylate copolymer (Eudragit ® E PO ReadyMix) | 34.00 |
| 7 | Purified Water* | — |

-continued

| Sr. # | Ingredient | mg/tab |
|---|---|---|
| | Coating 2 (non-functional) | |
| 8 | Opadry II Clear | 13.75 |
| 9 | Purified Water* | — |

*Purified water is not present in final product (evaporates during the processing).

A. Tablet core: Add Benzonatate gradually to Silicon Dioxide in a high shear mixer and mix to distribute uniformly. Sift the powder blend through a 600 micron screen and load into a blender. Weigh Isomalt, Microcrystalline cellulose and Polyethylene oxide and sift through a 600 micron screen. Add to the blender and mix for 10 minutes. Weigh Magnesium stearate and sift through a 250 micron screen. Add to the blend and mix for 5 minutes. Compress the tablets on a rotary tablet press using appropriate tooling to a target tablet weight of 425 mg at a tablet hardness of about 4-6 kp.

B. Coating 1: Add Eudragit E PO [Eudragit E PO Ready-Mix (Evonik) contains Butylated methacrylate copolymer, Sodium lauryl sulfate, Stearic acid, Talc, Silicon dioxide] to Purified water gradually under stirring using a propeller mixer and continue stirring for 60 minutes. Sift the coating dispersion through a 425 micron screen. Coat the core tablets with the coating dispersion in a perforated coating pan until 8% solid weight gain level using the specified process parameters as: Inlet temperature: 32° C.-40° C., Exhaust Temp.: 29° C.-34° C., Air flow: 58-64 cfm, Spray rate: 0.5-2.0 g/minutes.

Cure the coated tablets in a hot air oven at 40° C. for 2 hours.

C. Coating 2: Prepare the coating dispersion by dispersing the Opadry® II Clear powder [Opadry® II Clear (Colorcon) contains Polyvinyl alcohol, Polyethylene glycol, Talc] in Purified water under stirring. Continue stirring for 45 minutes. Sift the coating dispersion through a 425 micron sieve and carry out the coating of the Polyvinyl acetate coated tablets in a perforated coating pan for 3% solid weight gain level using the coating process parameters specified as: Inlet temperature: 62° C.-68° C., Exhaust Temp.: 42° C.-45° C., Air flow: 63-68 cfm, Spray rate: 0.5-1.5 g/minutes.

Example 17: Benzonatate Extended-Release Mini-Tabs, 30 mg

| Sr. # | Ingredient | Mg/tab |
|---|---|---|
| | Core Tablet | |
| 1 | Benzonatate, USP | 30.00 |
| 2 | Silicon Dioxide NF (Syloid ® XDP 3150) | 20.00 |
| 3 | Isomalt NF (Galen IQ 720) | 24.50 |
| 4 | Polyethylene Oxide NF (Polyox ® WSR 1105 NEO) | 40.00 |
| 5 | Magnesium Stearate NF | 0.50 |
| | Coating 1 (Bucco-Protective (Reverse Enteric)) | |
| 6 | Amino Methacrylate copolymer (Eudragit ® E PO ReadyMix) | 5.75 |
| 7 | Purified Water* | — |
| | Coating 2 (non-functional) | |
| 8 | Opadry II Clear | 3.62 |
| 9 | Purified Water* | — |

*Purified water is not present in final product (evaporates during processing).

A. Tablet core: Benzonatate is added gradually to Silicon Dioxide and mixed to distribute uniformly. The powder blend is passed through a 600 micron screen and loaded into a blender. Isomalt and Polyethylene oxide were passed through a 600 micron screen along with the Benzonatate-Silicon dioxide adsorbate and added to the blender. The blend is mixed for 10 minutes. Magnesium stearate (passed through a 250 micron screen) is added and lubricated for 5 minutes. Tablets are compressed on a rotary tablet press using appropriate tooling to a target tablet weight of 115 mg. Tablet hardness: 2-4 kp.

B. Coating 1: Eudragit® E PO [Eudragit® E PO Ready-Mix (Evonik) contains Butylated methacrylate copolymer, Sodium lauryl sulfate, Stearic acid, Talc, Silicon dioxide] is added to Purified water and mixed using a propeller mixer for 60 minutes. The coating dispersion is screened through a 425 micron screen. Coating is performed on the core tablets in a perforated coating pan until 8% solid weight gain level. The process parameters are as follows: Inlet temperature: 29° C.-32° C., Exhaust Temp.: 25° C.-28° C., Air flow: 58-62 cfm, Spray rate: 0.5-2.0 g/minutes. Tablets are allowed to cure in hot air oven at 40° C. for 2 hours.

C. Coating 2: The coating dispersion is prepared by adding Opadry® II Clear powder [Opadry® II Clear (Colorcon) contains Polyvinyl alcohol, Polyethylene glycol, Talc] to Purified water under stirring and further allowed to stir for 45 minutes. Coating is performed on the Eudragit® E PO coated tablets in a perforated coating pan. The coating process parameters are as follows: Inlet temperature: 58° C.-65° C., Exhaust Temp.: 39° C.-45° C., Air flow: 58-63 cfm, Spray rate: 0.5-1.2 g/minutes.

The coated tablets (five tablets, eq. to 150 mg are filled into size "0 el" hard gelatin capsule. Dissolution results in 0.1 N HCl at 37° C., USP Type II, Paddle, 50 rpm

| Time (h) | 1 | 2 | 4 | 8 |
|---|---|---|---|---|
| % Drug release (Example 5) | 24 | 58 | 90 | 100 |
| % Drug release (Example 6) | 28 | 52 | 92 | 97 |

An Open-Label, Randomized, Two-Period Cross-Over, Single-Day Pilot Study to Compare the Relative Bioavailability of Benzonatate Extended-Release Capsules with an Equivalent Dose of a Reference Product (Tessalon®) under Fasted Conditions in Healthy Adult Subjects (N=14) (Proposed PK Study)

Treatments

Treatment A: Test product, Benzonatate extended-release capsules. A 300 mg dose of the test product [2×150 mg capsules, each capsule containing five mini-tablets (Benzonatate extended-release tablets, 30 mg)] to be administered with 240 mL of potable water in 2 equal doses (300 mg each), at 0 and 12 hours under fasting conditions.

Treatment B: A 200 mg dose of the reference product (2 perles) to be administered in 3 equal doses (200 mg each), at 0, 8 and 16 hours under fasting conditions Dosing: Test Product: 2×150 mg b.i.d. (total 600 mg dose)

Reference Product: 2×100 mg t.i.d. (total 600 mg dose)
Processing: Collection of blood samples at a predetermined time points and analysis of the plasma samples for benzonatate conducted using a validated bioanalytical method followed by determination of PK parameters; mean plasma benzonatate $C_{max}$, $AUC_{0-inf}$ using a statistical software program.

All patents, patent publications, and other publications listed in this specification, are incorporated herein by reference in their entireties. While the invention has been described with reference to a particularly preferred embodiment, it will be appreciated that modifications can be made without departing from the spirit of the invention. Such modifications are intended to fall within the scope of the appended claims.

The invention claimed is:

1. A modified release benzonatate composition comprising a tablet or multiple mini-tablets in a capsule, wherein each mini-tablet or the tablet comprises: (a) a homogenous solid dispersion comprising (i) benzonatate adsorbed onto a porous silicon dioxide having a surface area of about 300 $m^2g$ to 350 $m^2g$ to form a benzonatate adsorbate powder, wherein the ratio of benzonatate to the silicon dioxide is about 4:1 to about 1:1, based on the weight of the adsorbate, and (ii) 20% w/w to 40% w/w of a water-soluble polyethylene oxide resin having an average molecular weight of about 900,000 as determined in a rheological method, based on the total weight of the solid dispersion (a), wherein (i) and (ii) are in a tablet or mini-tablets and form a matrix, (b) a bucco-protective pH-dependent, reverse enteric coat over said homogenous solid dispersion matrix tablet or mini-tablets and (c) a non-functional outer coat, wherein there is substantially no benzonatate release from the composition in a patient's buccal cavity post-dosing with the composition as assessed in simulated saliva, wherein said composition has an extended release of benzonatate of about 8 to about 12 hours, wherein the extended release can be assessed in an in vitro dissolution assay, and further wherein the modified release benzonatate composition is resistant to dose-dumping in the presence of alcoholic beverages.

2. The modified release benzonatate composition according to claim 1, wherein said reverse enteric coating comprises (a) a pH-dependent methyl methacrylate and diethylaminoethyl methacrylate copolymer or (b) a pH-dependent cationic copolymer based on dimethylaminoethyl methacrylate, butyl methacrylate and methyl methacrylate.

3. The modified release benzonatate composition according to claim 2, wherein said reverse enteric coating comprises (b) the pH-dependent cationic copolymer based on dimethylaminoethyl methacrylate, butyl methacrylate and methyl methacrylate.

4. The modified release benzonatate composition according to claim 3, wherein said reverse enteric coating comprises about 3% w/w to about 40% w/w based on the total weight of the tablet or mini-tablets.

5. The modified release benzonatate composition according to claim 3, wherein the weight ratio of benzonatate to silicon dioxide in the adsorbate powder is about 2:1.

6. The modified release benzonatate composition according to claim 3, wherein the weight ratio of benzonatate adsorbate powder to polyethylene oxide in the solid dispersion (a) is about 2 parts adsorbate to about 1 part polyethylene oxide.

7. The modified release benzonatate composition according to claim 3, wherein the polyethylene oxide is present in a concentration of 25% w/w to 35% w/w, based on the total weight of the dispersion (a) prior to coating.

8. The modified release benzonatate composition according to claim 3, wherein the composition has 75 mg to 300 mg benzonatate.

9. A method of delivering a daily dose of benzonatate to a patient in need thereof, the method comprising administering a modified release benzonatate composition according to claim 1 once per day.

\* \* \* \* \*